United States Patent
Lin et al.

(10) Patent No.: US 10,164,199 B2
(45) Date of Patent: *Dec. 25, 2018

(54) ORGANIC METAL COMPOUND AND ORGANIC LIGHT-EMITTING DEVICE EMPLOYING THE SAME

(71) Applicant: INDUSTRIAL TECHNOLOGY RESEARCH INSTITUTE, Hsinchu (TW)

(72) Inventors: Jin-Sheng Lin, Taipei (TW);
Cheng-An Wu, New Taipei (TW);
Pang-Chi Huang, Taoyuan (TW);
Meng-Hao Chang, New Taipei (TW);
Han-Cheng Yeh, Taipei (TW);
Chun-Neng Ku, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 468 days.

This patent is subject to a terminal disclaimer.

(21) Appl. No.: 14/837,844

(22) Filed: Aug. 27, 2015

(65) Prior Publication Data
US 2016/0164007 A1 Jun. 9, 2016

(30) Foreign Application Priority Data
Dec. 3, 2014 (TW) .............................. 103141945 A

(51) Int. Cl.
| | | |
|---|---|---|
| H01L 51/54 | (2006.01) |
| C09K 11/06 | (2006.01) |
| H01L 51/00 | (2006.01) |
| C07F 15/00 | (2006.01) |
| C09K 11/02 | (2006.01) |
| H01L 51/50 | (2006.01) |

(52) U.S. Cl.
CPC ...... *H01L 51/0085* (2013.01); *C07F 15/0033* (2013.01); *C09K 11/025* (2013.01); *C09K 11/06* (2013.01); *C09K 2211/1007* (2013.01); *C09K 2211/1037* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 6,830,828 B2* | 12/2004 | Thompson et al. | C07D 209/86 257/102 |
| 7,445,857 B2 | 11/2008 | Shen et al. | |
| 8,173,274 B2 | 5/2012 | Lin et al. | |
| 8,277,957 B2 | 10/2012 | Huang et al. | |
| 8,475,936 B2 | 7/2013 | Huang et al. | |
| 8,486,544 B2 | 7/2013 | Huang et al. | |
| 8,722,207 B2 | 5/2014 | Huang et al. | |
| 8,741,446 B2 | 6/2014 | Lin et al. | |
| 9,859,510 B2* | 1/2018 | Boudreault et al. | H01L 51/0085 |
| 9,954,189 B2* | 4/2018 | Chao et al. | H01L 51/0085 |
| 2001/0019782 A1* | 9/2001 | Igarashi et al. | C07F 15/0033 428/690 |
| 2003/0072964 A1 | 4/2003 | Kwong et al. | |
| 2006/0134462 A1* | 6/2006 | Yeh et al. | C07F 15/0033 428/690 |
| 2007/0237981 A1 | 10/2007 | Shen et al. | |
| 2010/0295032 A1 | 11/2010 | Kwong et al. | |
| 2011/0227049 A1 | 9/2011 | Xia et al. | |

(Continued)

FOREIGN PATENT DOCUMENTS

| | | |
|---|---|---|
| CN | 1589307 A | 3/2005 |
| CN | 1803970 A | 7/2006 |

(Continued)

OTHER PUBLICATIONS

Chang et al., "Unmodified small-molecule organic light-emitting diodes by blade coating", Elsevier, Organic Electronics, vol. 13, 2012, pp. 2149-2155.

Fan et al., "Highly efficient, solution-processed orange-red phosphorescent OLEDs by using new iridium phosphor with thieno[3,2-c] pyridine derivative as cyclometalating ligand", Elsevier, Organic Electronics, vol. 14, 2013, pp. 3392-3398.

Huang et al., "Uniform dispersion of triplet emitters in multi-layer solution-processed organic light-emitting diodes", Elsevier, Synthetic Metals, vol. 160, 2010, pp. 2393-2396.

Jung et al., "Synthesis and Crystal Structure of Blue Phosphorescent mer-Tris(2',6'-difluoro-2,3'-bipyridinato-N, $C^{4'}$) Iridium (III)", Bull. Korean Chem. Soc., vol. 33, No. 1, 2012, pp. 183-188.

(Continued)

*Primary Examiner* — Marie R. Yamnitzky
(74) *Attorney, Agent, or Firm* — Birch, Stewart, Kolasch & Birch, LLP

(57) ABSTRACT

Organic metal compounds, and organic light-emitting devices employing the same, are provided. The organic metal compound has a chemical structure represented by formula (I):

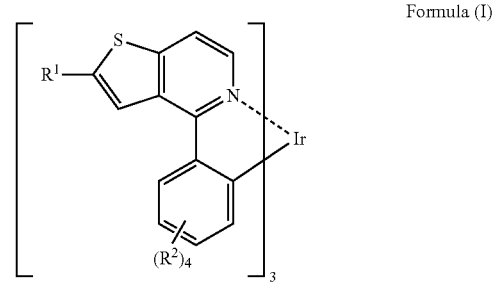

Formula (I)

wherein each $R^1$ can be independently hydrogen, $C_{1-12}$ alkyl group, $C_{5-10}$ cycloalkyl group, $C_{3-12}$ heteroaryl group, or $C_{6-12}$ aryl group; $R^2$ can be independently hydrogen, halogen, $C_{1-12}$ alkyl group, $C_{5-10}$ cycloalkyl group, $C_{3-12}$ heteroaryl group, or $C_{6-12}$ aryl group.

12 Claims, 2 Drawing Sheets

(56) References Cited

U.S. PATENT DOCUMENTS

| | | |
|---|---|---|
| 2011/0284799 A1 | 11/2011 | Stoessel et al. |
| 2011/0285275 A1 | 11/2011 | Huang et al. |
| 2012/0061654 A1 | 3/2012 | Rayabarapu et al. |
| 2012/0119190 A1 | 5/2012 | Alleyne et al. |
| 2012/0181511 A1 | 7/2012 | Ma et al. |
| 2012/0212126 A1 | 8/2012 | Tsai et al. |
| 2012/0217868 A1 | 8/2012 | Ma et al. |
| 2013/0033171 A1 | 2/2013 | Huang et al. |
| 2013/0126831 A1 | 5/2013 | Ma et al. |
| 2013/0146848 A1 | 6/2013 | Ma et al. |
| 2014/0103305 A1 | 4/2014 | Ma et al. |
| 2015/0188060 A1* | 7/2015 | Chao et al. .............. C09K 11/06 257/40 |
| 2016/0164006 A1* | 6/2016 | Chao et al. ......... H01L 51/0085 257/40 |

FOREIGN PATENT DOCUMENTS

| | | |
|---|---|---|
| CN | 102190618 A | 9/2011 |
| CN | 102453027 A | 5/2012 |
| CN | 102911211 A | 2/2013 |
| CN | 102952162 A | 3/2013 |
| CN | 103298907 A | 9/2013 |
| CN | 101659638 B | 10/2013 |
| CN | 102282150 B | 7/2015 |
| KR | 10-2014-0124654 A | 10/2014 |
| TW | I242999 B | 11/2005 |
| TW | 200621934 A | 7/2006 |
| TW | 200623955 A | 7/2006 |
| TW | 201130948 A1 | 9/2011 |
| TW | 201141987 A1 | 12/2011 |
| TW | 201224114 A1 | 6/2012 |
| TW | 201233674 A1 | 8/2012 |
| TW | 201241152 A1 | 10/2012 |
| TW | 201307326 A1 | 2/2013 |
| TW | I385235 B | 2/2013 |
| TW | 201309714 A1 | 3/2013 |
| TW | I395804 B1 | 5/2013 |
| TW | 201326183 A1 | 7/2013 |
| TW | 201329199 A1 | 7/2013 |
| TW | 201329203 A1 | 7/2013 |
| TW | I402259 B1 | 7/2013 |
| TW | I421255 B | 1/2014 |
| TW | I425076 B | 2/2014 |
| TW | I429652 B | 3/2014 |
| TW | I431003 B | 3/2014 |
| TW | I454450 B | 10/2014 |
| TW | 201446775 A1 | 12/2014 |
| TW | I471308 B | 2/2015 |
| TW | 201518472 A | 5/2015 |
| WO | WO 2010/111175 A1 | 9/2010 |
| WO | WO 2010/118029 A1 | 10/2010 |

OTHER PUBLICATIONS

Lee et al., "Blue Phosphorescent Ir(III) Complex with High Color Purity: fac-Tris(2',6'-difluoro-2,3'-bipyridinato-N,$C^{4'}$)iridium(III)", Inorganic Chemistry, vol. 48, 2009, pp. 1030-1037.

Lo et al., "Solution-Processible Phosphorescent Blue Dendrimers Based on Biphenyl-Dendrons and Fac-tris(phenyltriazolyl)iridium(III) Cores", Advanced Functional Materials, vol. 18, 2008, pp. 3080-3090.

Pu et al., "fac-Tris(2-phenylpyridine)iridium (III)s, covalently surrounded by six bulky host dendrons, for a highly efficient solution-processed organic light emitting device", Elsevier, Organic Electronics, vol. 12, 2011, pp. 2103-2110.

Tamayo et al., Synthesis and Characterization of Facial and Meridional Tris-cyclometalated Iridium(III) Complexes, Journal of the American Chemical Society, vol. 125, No. 24, 2003, pp. 7377-7387.

* cited by examiner

ORGANIC METAL COMPOUND AND ORGANIC LIGHT-EMITTING DEVICE EMPLOYING THE SAME

CROSS REFERENCE TO RELATED APPLICATION

The application is based on, and claims priority from, Taiwan Application Serial Number 103141945, filed on Dec. 3, 2014, the disclosure of which is hereby incorporated by reference herein in its entirety.

TECHNICAL FIELD

The disclosure relates to an organic metal compound and an organic light-emitting device employing the same.

BACKGROUND

An organic light-emitting diode (OLED) is a light-emitting diode employing an organic electroluminescent layer as an active layer. OLED display devices have high luminescent efficiency and long operating lifespans. In comparison with liquid-crystal displays, due to the characteristic of spontaneous emission, a device employing an organic light-emitting diode is free of a back-light source.

Generally, an organic light-emitting device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton, which results from the recombination of the hole and electron, can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of an OLED.

SUMMARY

According to an embodiment of the disclosure, the disclosure provides an organic metal compound having a structure of Formula (I):

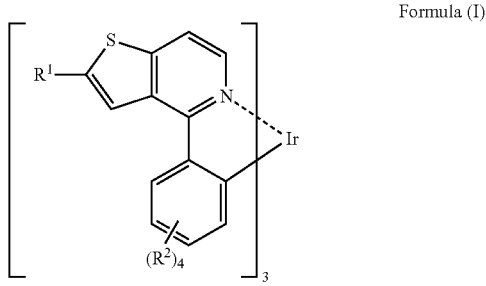

Formula (I)

wherein, $R^1$ is independently hydrogen, $C_{1-12}$ alkyl group, $C_{5-10}$ cycloalkyl group, $C_{3-12}$ heteroaryl group, or $C_{6-12}$ aryl group; $R^2$ is independently hydrogen, halogen, $C_{1-12}$ alkyl group, $C_{5-10}$ cycloalkyl group, $C_{3-12}$ heteroaryl group, or $C_{6-12}$ aryl group.

According to another embodiment of the disclosure, the disclosure provides an organic light-emitting device. The device includes a pair of electrodes and an organic light-emitting element, disposed between the electrodes, wherein the organic light-emitting element includes the aforementioned organic metal compound.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
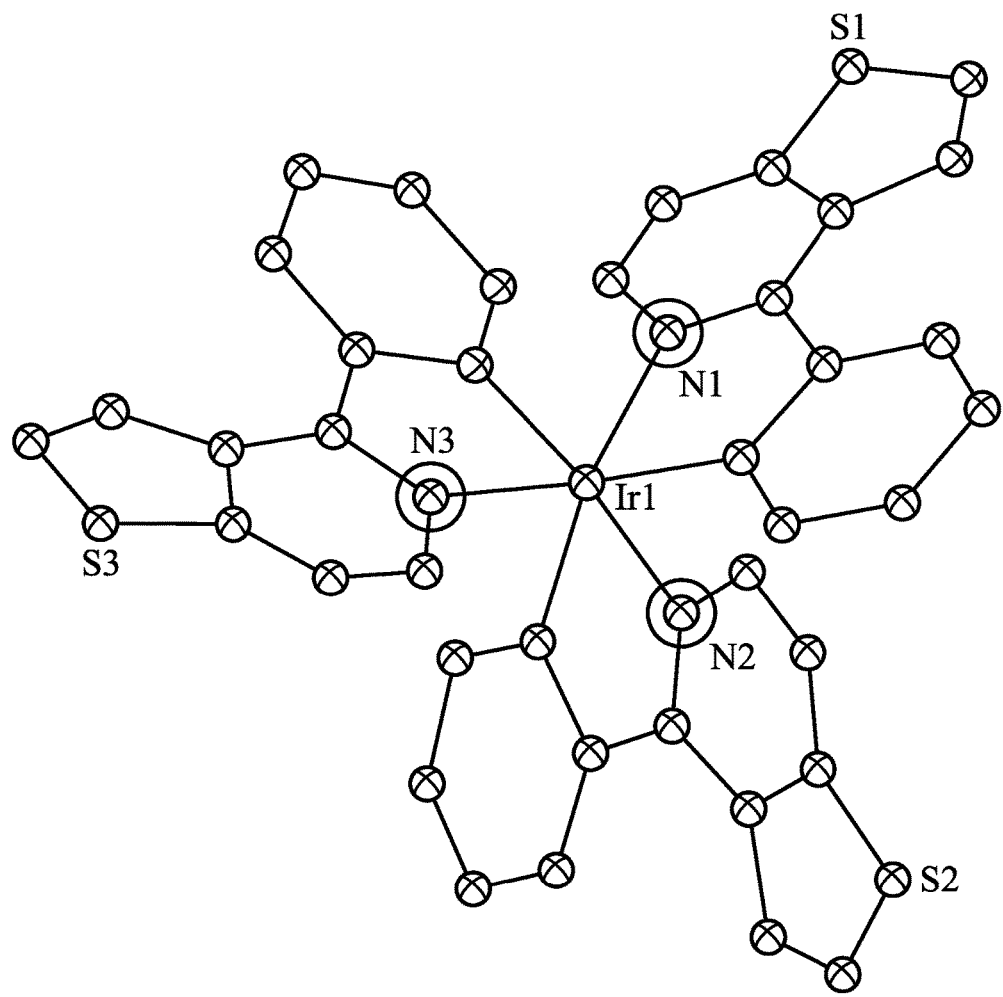
FIG. 1 is a Single-Crystal X-ray diffraction pattern of the organic metal compound obtained in Example 1.

The following description is of the best-contemplated mode of carrying out the disclosure. This description is made for the purpose of illustrating the general principles of the disclosure and should not be taken in a limiting sense. The scope of the disclosure is best determined by reference to the appended claims.

Organic Metal Compound

The disclosure provides an organic metal compound and an organic light-emitting device employing the same. The organic metal compound can be a tris-facial six-coordinate iridium compound including specific thienopyridine-based ligand, such as thieno[3,2-c]pyridine-based derivative ligand. Since the thermal stability can be enhanced by means of the bondings between iridium and ligands, the organic metal compound of the disclosure can have a thermal degradation temperature ($T_d$) that is higher than about 400° C. Therefore, the organic metal compound having Formula (I) of the disclosure is suitable for being purified by a sublimation process (the organic metal compound having Formula (I) of the disclosure has a sublimation yield that is higher than about 80%). In addition, due to the specific chemical structure, the organic metal compound of the disclosure can have a suitable highest occupied molecular orbital (HOMO) and lowest unoccupied molecular orbital (LUMO) energy gap (between about 6.0 eV and 3.0 eV), thereby facilitating the electrons recombining with the holes to form excitons, and resulting in luminescence. Therefore, the organic metal compound having Formula (I) of the disclosure can serve as phosphorescence light-emitting material for enhancing the luminous efficiency of the organic light-emitting device employing the same.

According to an embodiment of the disclosure, the disclosure provides an organic metal compound having a structure of Formula (I):

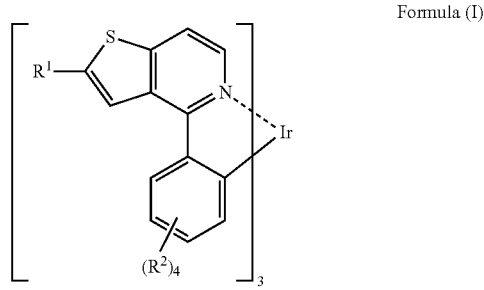

Formula (I)

wherein, $R^1$ is independently hydrogen, $C_{1-12}$ alkyl group, $C_{5-10}$ cycloalkyl group, $C_{3-12}$ heteroaryl group, or $C_{6-12}$ aryl group; $R^2$ is independently hydrogen, halogen, $C_{1-12}$ alkyl group, $C_{5-10}$ cycloalkyl group, $C_{3-12}$ heteroaryl group, or $C_{6-12}$ aryl group.

The organic metal compounds of the disclosure can serve as a green or yellow phosphorescent dopant material (having a maximum luminous intensity peak of between about 520 nm to 570 nm), and can be applied to an organic light-emitting device for enhancing the luminous efficiency.

According to an embodiment of the disclosure, each $R^1$ is independently hydrogen, methyl, ethyl, propyl, isopropyl, n-butyl group, isobutyl group, sec-butyl group, tert-butyl group, pentyl group, hexyl group, cyclohexyl group, cyclopentyl group, octyl group, decyl group, dodecyl group, phenyl group, biphenyl group, or naphthyl.

In Formula (I), the structure

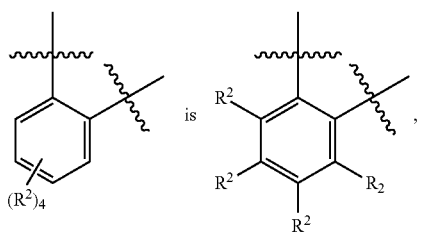

and $R^2$ are independent. According to an embodiment of the disclosure, each $R^2$ can be independently hydrogen, fluorine, methyl, ethyl, propyl, isopropyl, n-butyl group, isobutyl group, sec-butyl group, tert-butyl group, pentyl group, hexyl group, cyclohexyl group, cyclopentyl group, octyl group, decyl group, dodecyl group, phenyl group, biphenyl group, or naphthyl.

According to some embodiments of the disclosure, at least one of $R^1$ and $R^2$ of the organic metal compound having the structure of Formula (I) is not hydrogen. According to some embodiments of the disclosure, at least one of $R^2$ of the organic metal compound having the structure of Formula (I) is not hydrogen. According to some embodiments of the disclosure, $R^1$ of the organic metal compound having the structure of Formula (I) is not hydrogen and at least one of $R^2$ of the organic metal compound having the structure of Formula (I) is not hydrogen.

According to some embodiments of the disclosure, the organic metal compound can have a structure of Formula (II):

Formula (II)

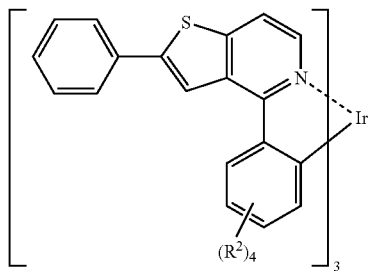

wherein, $R^2$ is independently hydrogen, halogen, $C_{1-12}$ alkyl group, $C_{5-10}$ cycloalkyl group, $C_{3-12}$ heteroaryl group, or $C_{6-12}$ aryl group. The organic metal compound having a structure of Formula (II) can be

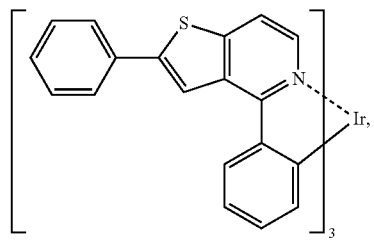

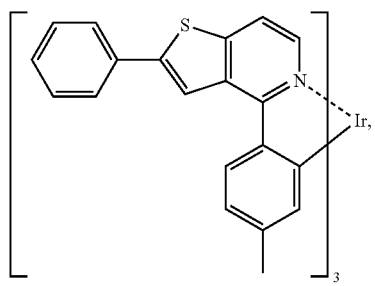

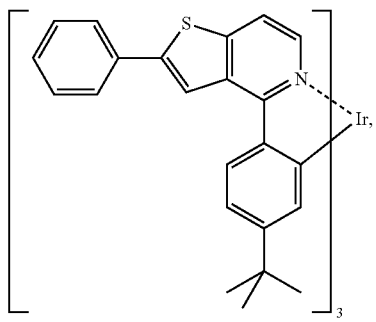

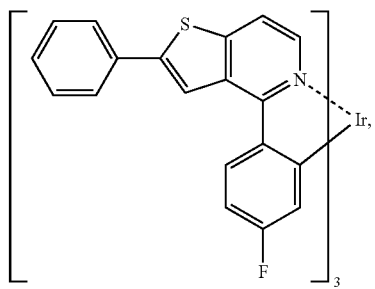

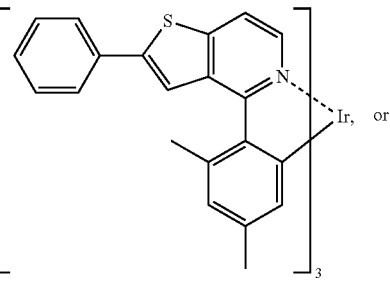

-continued

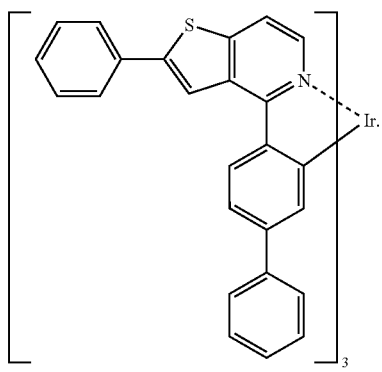

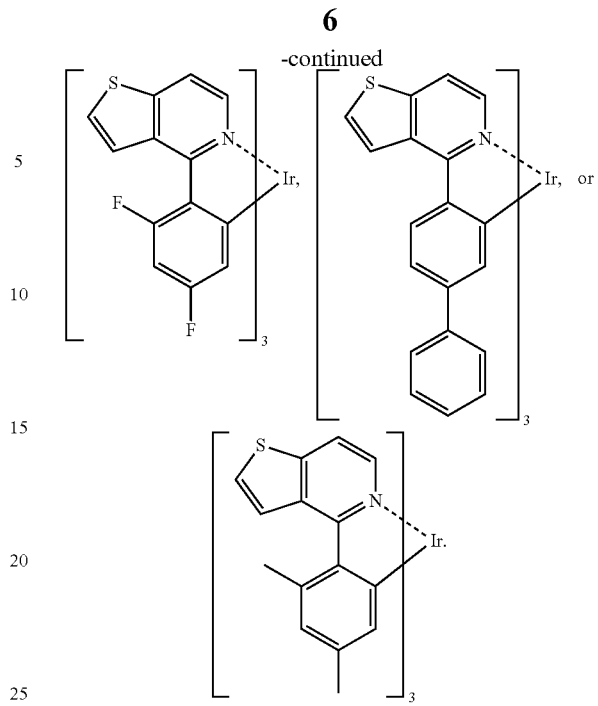

According to some embodiments of the disclosure, the organic metal compound can have a structure of Formula (III):

Formula (III)

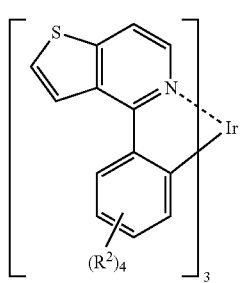

wherein, $R^2$ is independently hydrogen, halogen, $C_{1-12}$ alkyl group, $C_{5-10}$ cycloalkyl group, $C_{3-12}$ heteroaryl group, or $C_{6-12}$ aryl group. The organic metal compound having a structure of Formula (III) can be According to some embodiments of the disclosure, the organic metal compound can have a structure of (IV):

Formula (IV)

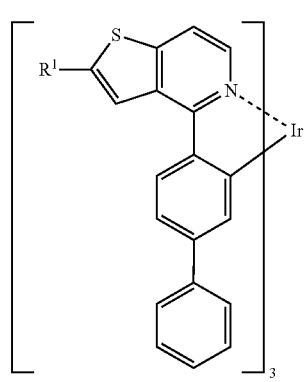

wherein, $R^1$ is independently hydrogen, $C_{1-12}$ alkyl group, $C_{5-10}$ cycloalkyl group, $C_{3-12}$ heteroaryl group, or $C_{6-12}$ aryl group. The organic metal compound having a structure of Formula (IV) can be

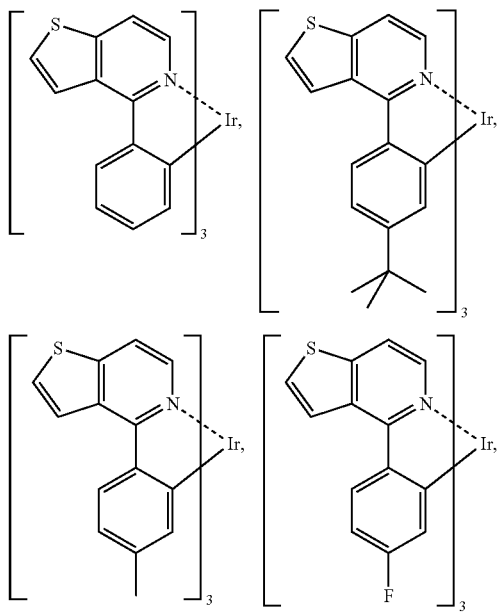

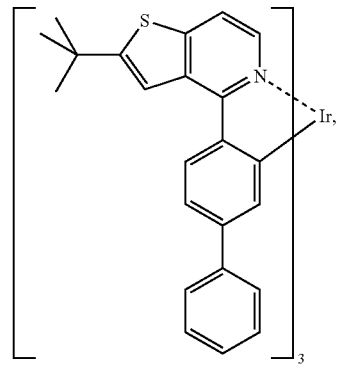

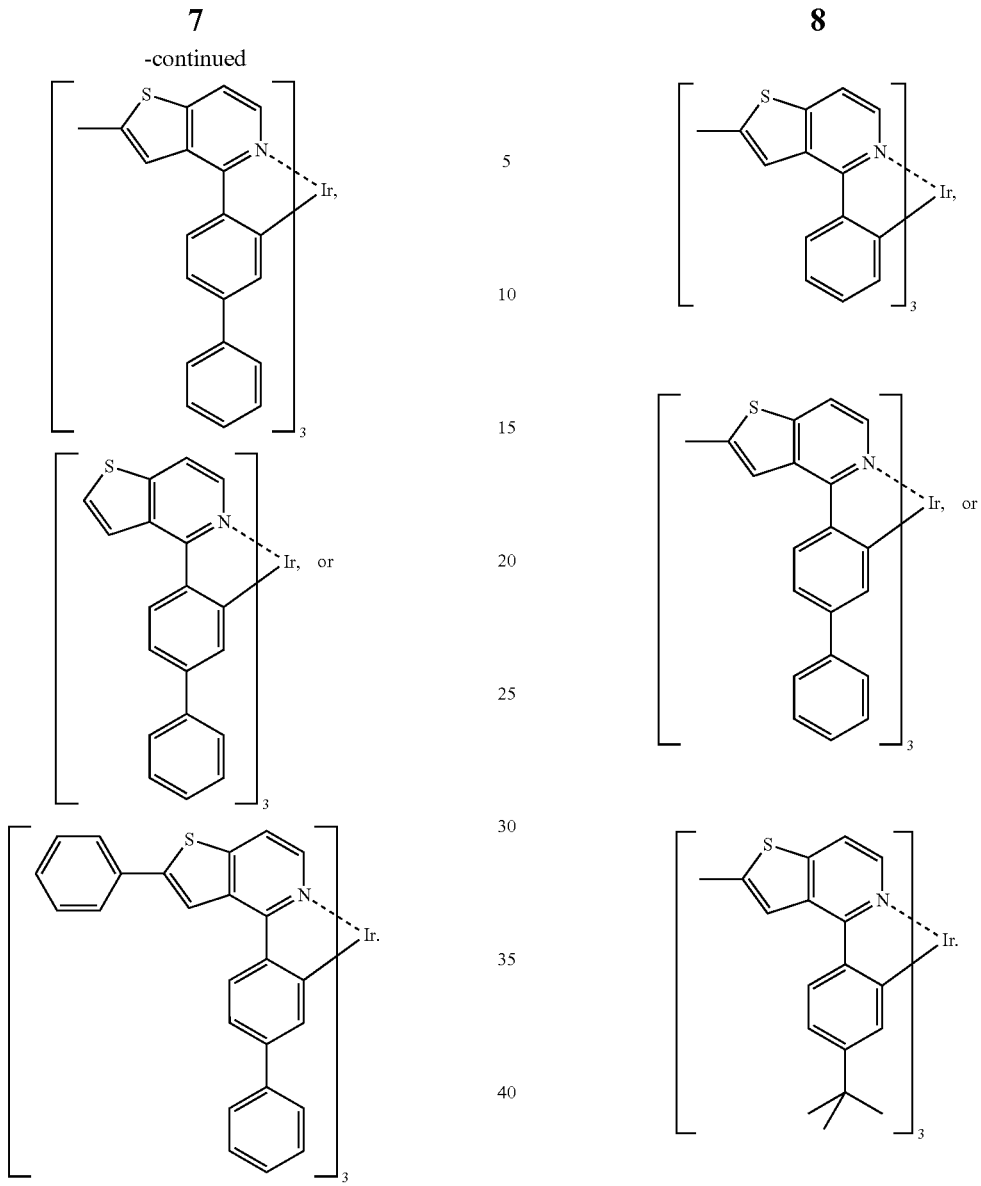

According to some embodiments of the disclosure, the organic metal compound can have a structure of Formula (V):

Formula (V)

According to some embodiments of the disclosure, the organic metal compound can have a structure of Formula (VI):

Formula (VI)

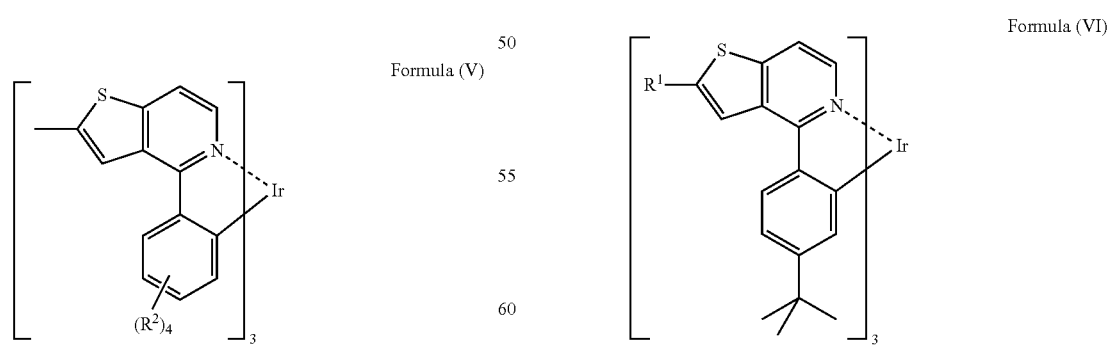

wherein, $R^1$ is independently hydrogen, $C_{1-12}$ alkyl group, $C_{5-10}$ cycloalkyl group, $C_{3-12}$ heteroaryl group, or $C_{6-12}$ aryl group. The organic metal compound having a structure of Formula (V) can be wherein, $R^1$ is independently hydrogen, $C_{1-12}$ alkyl group, $C_{5-10}$ cycloalkyl group, $C_{3-12}$ heteroaryl group, or $C_{6-12}$ aryl group. The organic metal compound having a structure of Formula (VI) can be

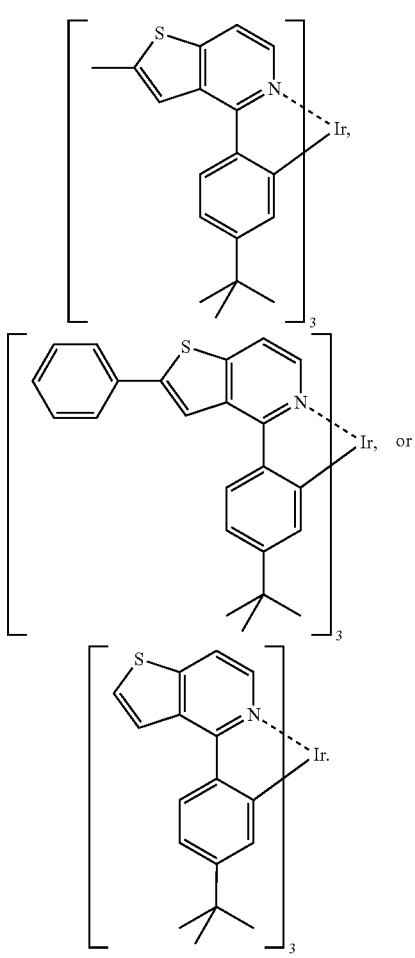

The following examples are intended to illustrate the disclosure more fully without limiting the scope, since numerous modifications and variations will be apparent to those skilled in this art.

Example 1: Preparation of Organic Metal Compound (I)

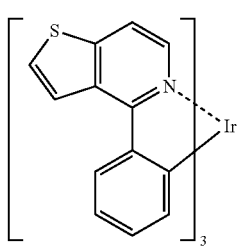

Organic Metal Compound (I)

9.0 g of 2-(2-aminoethyl)thiophene (70.9 mmol) and 40 mL of water were added into a reaction bottle. Next, 11 mL of benzoyl chloride and 45 mL of sodium hydroxide aqueous solution (20 wt %) were added into the reaction bottle at 0° C., and a white powder product was separated out during the reaction. Next, after reacting for 12 hours, the mixture was filtrated and the filter cake was collected. Next, the filter cake was ground to fine powders and washed with water and hexane, obtaining Compound (1) with a yield of 95%. The synthesis pathway of the above reaction was as follows:

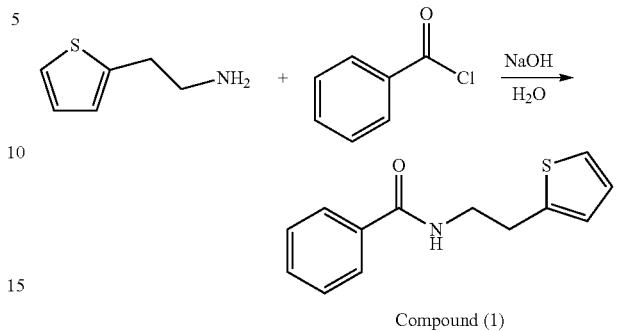

Compound (1)

The physical measurement of the compound (1) is listed below: $^1$H NMR (200 MHz, CDCl$_3$, 294 K): δ 8.81 (d, 2H), 7.47~7.30 (m, 4H), 7.11 (d, 1H), 7.91 (t, 1H), 6.80 (d, 1H), 3.66 (q, 2H), 3.10 (t, 2H).

11.6 g of Compound (1) (50 mmol) and 50 mL of toluene were added into a reaction bottle and the reaction bottle was cooled to 0° C. Next, 11.5 g of phosphoryl chloride (POCl$_3$, 75 mmol) was slowly added into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate (EA) and water as the extraction solvent. Next, an organic phase was separated and concentrated, and then purified by column chromatography, obtaining Compound (2) with a yield of 75%. The synthesis pathway of the above reaction was as follows:

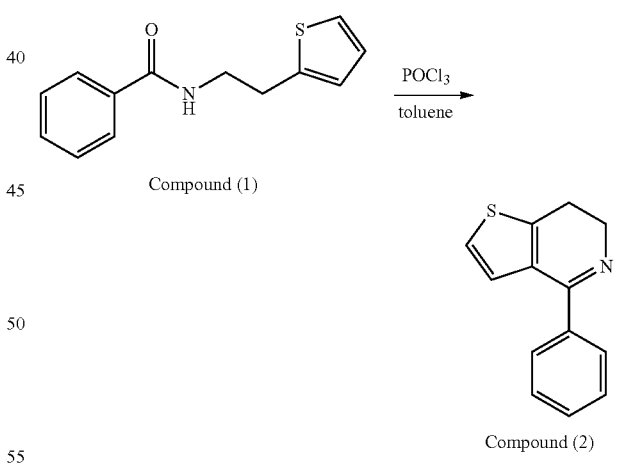

Compound (2)

The physical measurement of the compound (2) is listed below: $^1$H NMR (200 MHz, CDCl$_3$, 294 K): δ 7.50 (d, 2H), 7.30~7.22 (m, 3H), 6.91 (d, 1H), 6.84 (d, 1H), 3.78 (t, 2H), 2.76 (t, 2H).

10.6 g of Compound (2) (50 mmol), 10 g of palladium 10% on carbon (Pd/C catalyst), and 50 mL of toluene were added into a reaction bottle. Next, the reaction bottle was heated to reflux. Next, after removing Pd/C catalyst by filtration, the filtrate was extracted three times using ethyl acetate (EA) and water as the extraction solvent, and an organic phase was separated and concentrated, and then purified by column chromatography, obtaining Compound (3) with a yield of 95%. The synthesis pathway of the above reaction was as follows:

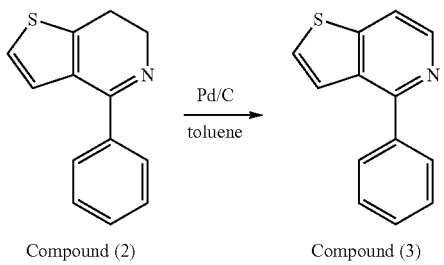

Compound (2)    Compound (3)

The physical measurement of the compound (3) is listed below: $^1$H NMR (200 MHz, CDCl$_3$, 294 K): δ 8.53 (d, 1H), 7.81 (d, 2H), 7.77 (d, 1H), 7.60~7.40 (m, 5H).

Next, 28 mg of Compound (3) (4.4 mmol), and 598 mg of IrCl$_3$ (2 mmol), 15 mL of 2-methoxyethanol, and 5 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (4) with a yield of 72%. The synthesis pathway of the above reaction was as follows:

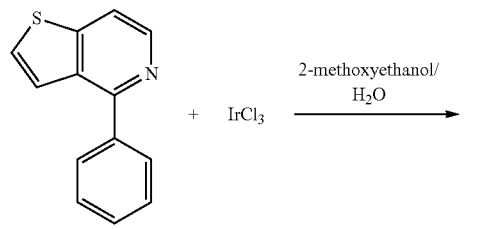

Compound (3)

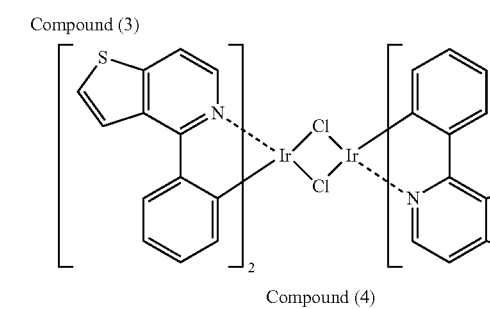

Compound (4)

Next, 1.3 g of Compound (4) (1 mmol), acetyl acetone, 300 mg, 3 mmol), 212 mg of sodium carbonate (Na$_2$CO$_3$, 2 mmol), and 2-methoxyethanol (20 mL) were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (5) with a yield of 72%. The synthesis pathway of the above reaction was as follows:

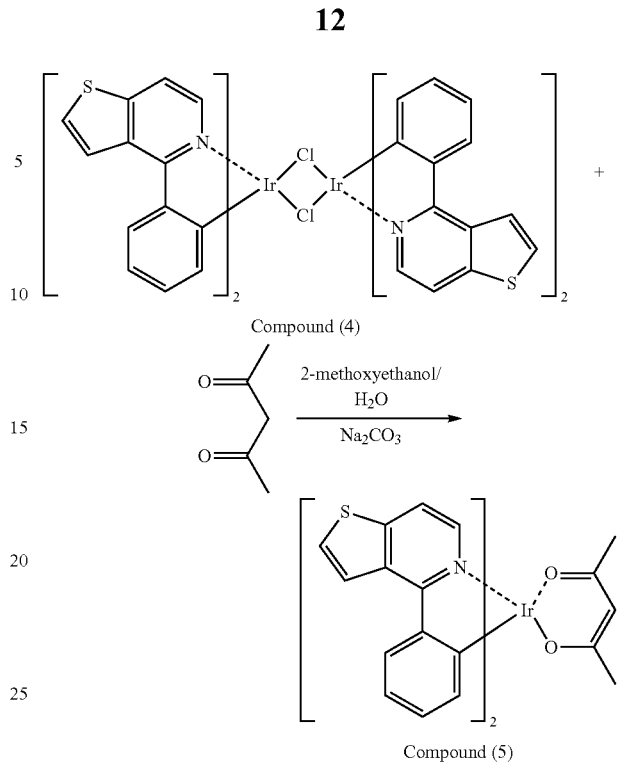

Compound (4)

Compound (5)

The physical measurement of the compound (5) is listed below: $^1$H NMR (200 MHz, CDCl$_3$, 294 K): δ 8.52 (d, 2H), 8.13 (d, 2H), 7.87 (d, 2H), 7.68 (d, 2H), 7.59 (d, 2H), 6.99 (t, 2H), 6.69 (t, 2H), 6.29 (d, 2H), 5.33 (s, 1H), 1.82 (s, 6H).

711 mg of Compound (5) (1 mmol), 422 mg of Compound (3) (2 mmol), and 10 mL of glycerol were added into a reaction bottle. Next, after removing moisture and purging nitrogen gas several times, the reaction bottle was heated to 200° C. After reacting for 48 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (I). The synthesis pathway of the above reaction was as follows:

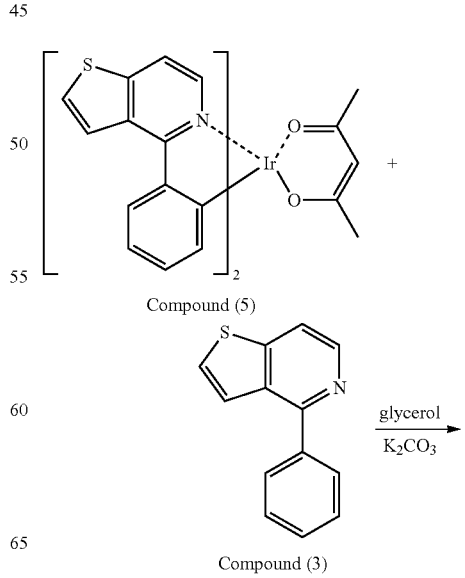

Compound (5)

Compound (3)

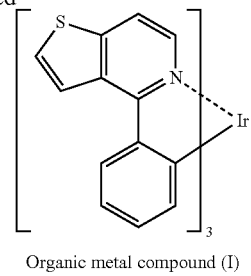

Organic metal compound (I)

The physical measurement of the organic metal compound (I) is listed below: $^1$H NMR (200 MHz, CDCl$_3$, 294 K): δ 8.35 (d, 3H), 8.22 (d, 3H), 7.51 (d, 3H), 7.34 (m, 6H), 6.90 (m, 9H). Elemental analysis: C$_{39}$H$_{24}$IrN$_3$S$_3$: N, 5.11; C, 56.91; H, 2.94. Found: N, 5.09; C, 56.88; H, 2.97.

Organic metal compound (I) was analyzed by X-ray diffraction spectroscopy, and the result was shown in FIG. 1.

As the result of NMR and X-ray diffraction spectroscopy, Organic metal compound (I) of Example 1 has a facial arrangement.

Comparative Example 1

Compound (3) (6.6 mmol), IrCl$_3$ (2 mmol), and glycerol were added into a reaction bottle. Next, after removing moisture and purging nitrogen gas several times, the reaction bottle was heated to 200° C. After reacting for 12 hours, the reaction bottle was cooled to room temperature, and a black precipitate was obtained. After analyzing the black precipitate, iridium organic compound was not obtained since the iridium intermediate was apt to be decomposed.

Comparative Example 2

Compound (4) (0.5 mmol), Compound (3) (1 mmol), 138 mg of potassium carbonate (K$_2$CO$_3$, 1 mmol), and 10 mL of glycerol were added into a reaction bottle. Next, After removing moisture and purging nitrogen gas several times, the reaction bottle was heated to 200° C. After reacting for 48 hours, the reaction bottle was cooled to room temperature, and a black precipitate was obtained. After analyzing the black precipitate, iridium organic compound was not obtained since the iridium intermediate was apt to be decomposed.

Example 2: Preparation of Organic Metal Compound (II)

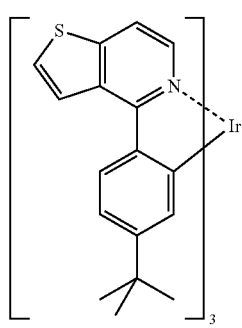

Organic metal compound (II)

76.3 g of 2-(2-aminoethyl)thiophene (600 mmol) and 1 L of water were added into a reaction bottle. Next, 91 mL of 4-tert-butylbenzoyl chloride (500 mmol) and sodium hydroxide aqueous solution (20 wt %, 150 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining compound (6) with a yield of 99%. The synthesis pathway of the above reaction was as follows:

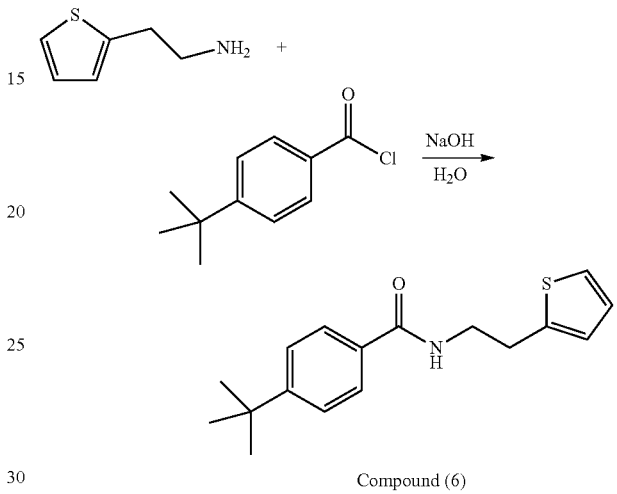

Compound (6)

50 g of compound (6)(174 mmol) and 170 mL of toluene were added into a reaction bottle, and the reaction bottle was cooled to 0° C. Next, 17 mL of phosphoryl chloride (POCl$_3$, 174 mmol). After the addition was complete, the reaction bottle was heated to reflux. After reacting for 12 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (7) with a yield of 72%. The synthesis pathway of the above reaction was as follows:

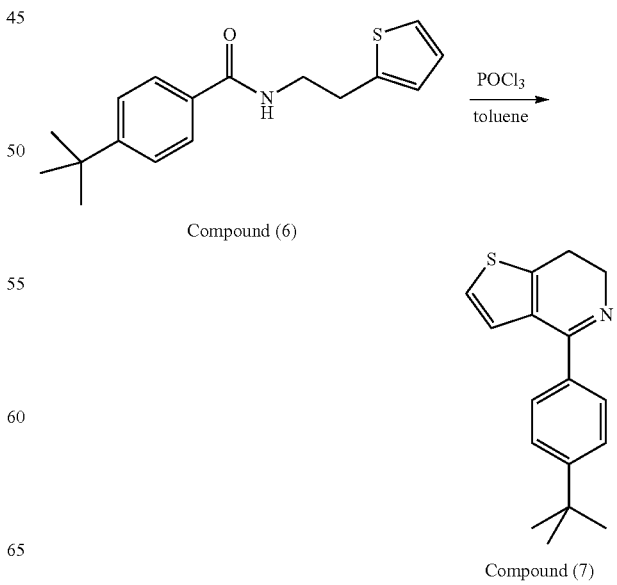

Compound (6)

Compound (7)

46 g of Compound (7) (174 mmol), 50 g of Pd/C catalyst (palladium 10% on carbon), and 170 mL of toluene were added into a reaction bottle. Next, the reaction bottle was heated to reflux for 48 hours. Next, after removing Pd/C catalyst by filtration, the filtrate was extracted three times using ethyl acetate and water. Next, an organic phase was separated and concentrated, and then purified by column chromatography, obtaining Compound (8) with a yield of 90%. The synthesis pathway of the above reaction was as follows:

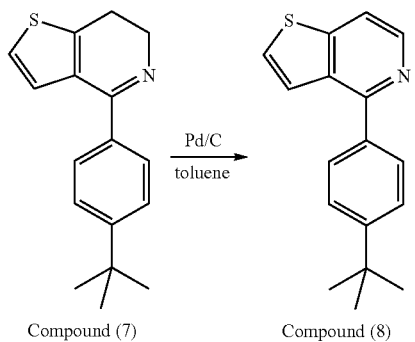 [SMILES: CC(C)(C)c1ccc(C2=NCCc3sccc32)cc1 ; CC(C)(C)c1ccc(-c2nccc3sccc23)cc1]

Next, Compound (8) (18.7 g, 70 mmol), 10.4 g of IrCl$_3$ (35 mmol), 262 mL of 2-methoxyethanol, and 88 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (9) with a yield of 90%. The synthesis pathway of the above reaction was as follows:

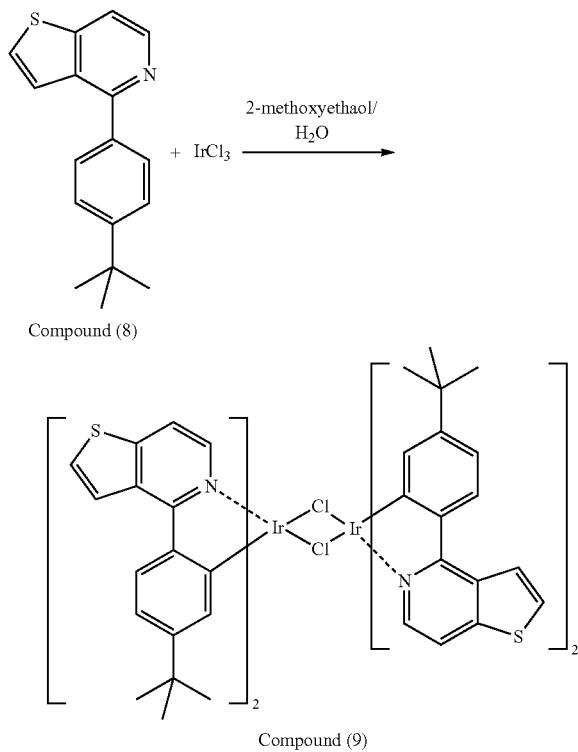

Next, 26.6 g of Compound (9) (17.5 mmol), 7 g of acetyl acetone (70 mmol), 7.4 g of sodium carbonate (Na$_2$CO$_3$, 70 mmol), and 175 mL of 2-methoxyethanol were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (10) with a yield of 64%. The synthesis pathway of the above reaction was as follows:

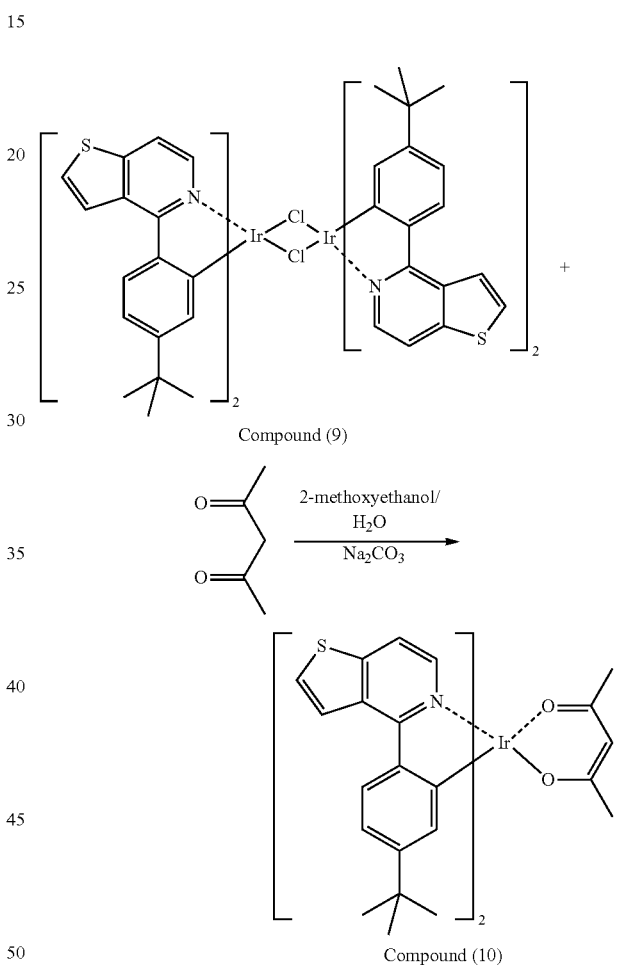

18.3 g of Compound (10) (22.2 mmol), 11.9 g of Compound (8) (44.5 mmol), and 220 mL of glycerol were added into a reaction bottle. Next, after removing moisture and purging nitrogen gas several times, the reaction bottle was heated to 200° C. After reacting for 48 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (II). The synthesis pathway of the above reaction was as follows:

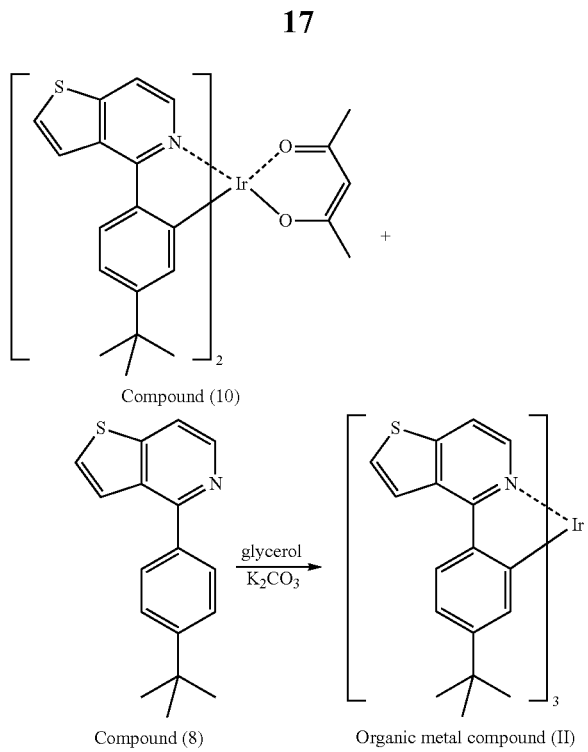

Compound (10)

Compound (8)    Organic metal compound (II)

Example 3: Preparation of Organic Metal Compound (III)

Organic metal compound (III)

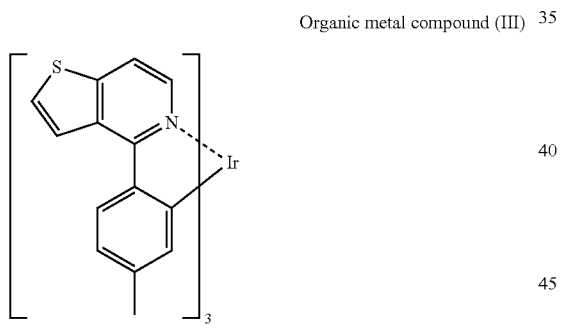

30.0 g of 2-(2-aminoethyl)thiophene (235.8 mmol), and 500 mL of water were added into a reaction bottle. Next, 40.1 g of 4-methyl-benzoyl chloride (259.4 mmol) and sodium hydroxide aqueous solution (20 wt %, 200 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (11) with a yield of 89%. The synthesis pathway of the above reaction was as follows:

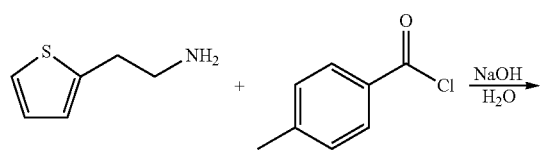

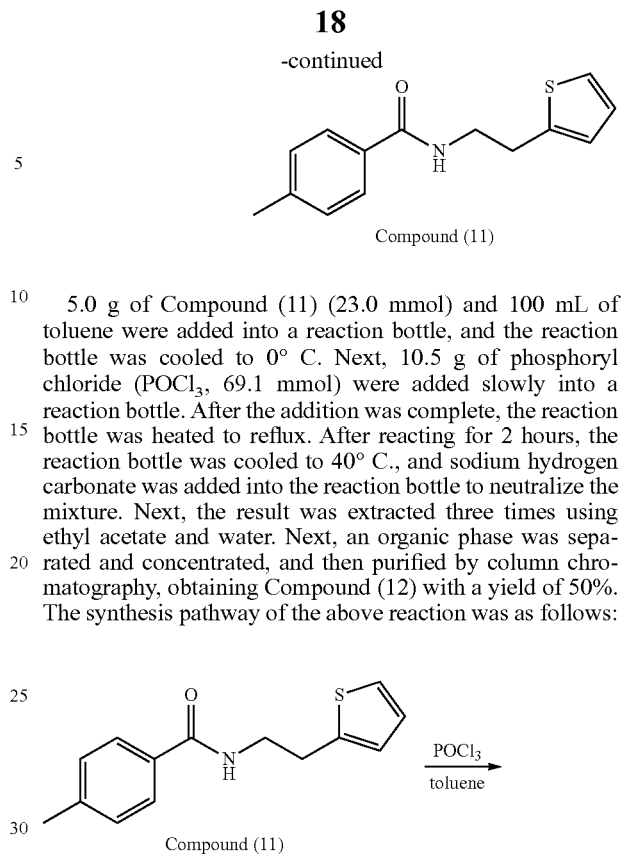

Compound (11)

5.0 g of Compound (11) (23.0 mmol) and 100 mL of toluene were added into a reaction bottle, and the reaction bottle was cooled to 0° C. Next, 10.5 g of phosphoryl chloride (POCl$_3$, 69.1 mmol) were added slowly into a reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (12) with a yield of 50%. The synthesis pathway of the above reaction was as follows:

Compound (11)

Compound (12)

5.0 g of Compound (12) (22.0 mmol), 5 g of Pd/C catalyst (palladium 10% on carbon), and 30 mL of toluene were added into a reaction bottle. Next, the reaction bottle was heated to reflux for 24 hours. Next, after removing Pd/C catalyst by filtration, the filtrate was extracted three times using ethyl acetate and water. Next, an organic phase was separated and concentrated, and then purified by column chromatography, obtaining Compound (13) with a yield of 83%. The synthesis pathway of the above reaction was as follows:

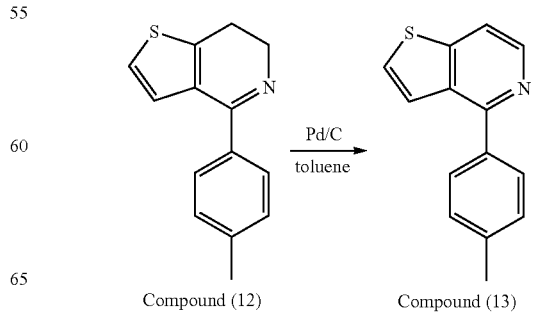

Compound (12)    Compound (13)

Next, compound (13) (1 g, 4.4 mmol), and 630 mg of IrCl₃ (2.1 mmol), 30 mL of 2-methoxyethanol, and 10 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (14) with a yield of 73%. The synthesis pathway of the above reaction was as follows:

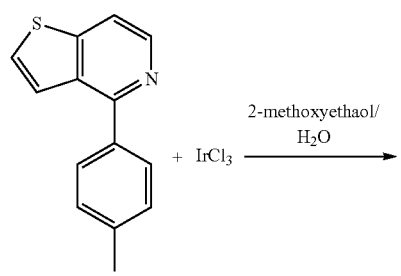

Compound (13)

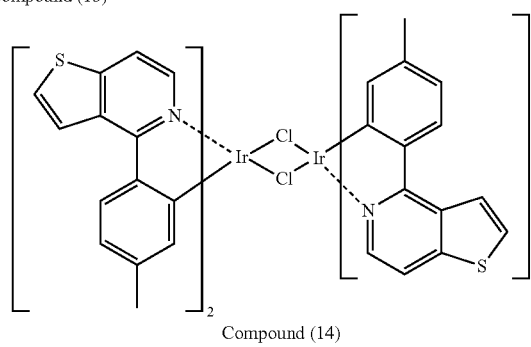

Compound (14)

Next, 1.04 g of Compound (14) (0.77 mmol), 230 mg of acetyl acetone (2.3 mmol), sodium carbonate (Na₂CO₃, 250 mg, 2.3 mmol), and 30 mL of 2-methoxyethanol were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (15) with a yield of 74%. The synthesis pathway of the above reaction was as follows:

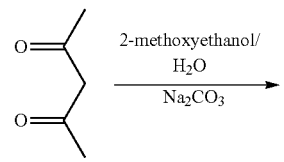

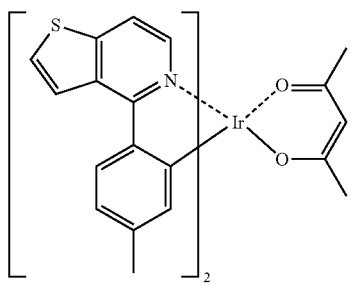

Compound (15)

3.0 g of Compound (15) (4.05 mmol), 1.82 g of Compound (13) (8.1 mmol), and 15 mL of glycerol were added into a reaction bottle. Next, after removing moisture and purging nitrogen gas several times, the reaction bottle was heated to 200° C. After reacting for 48 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (III). The synthesis pathway of the above reaction was as follows:

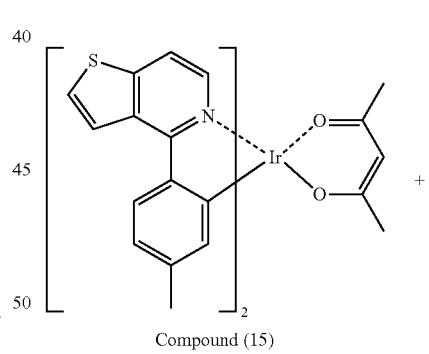

Compound (15)

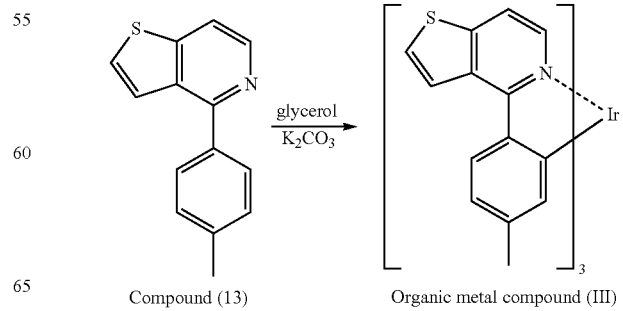

Compound (13)          Organic metal compound (III)

Example 4: Preparation of Organic Metal Compound (IV)

Organic metal compound (IV)

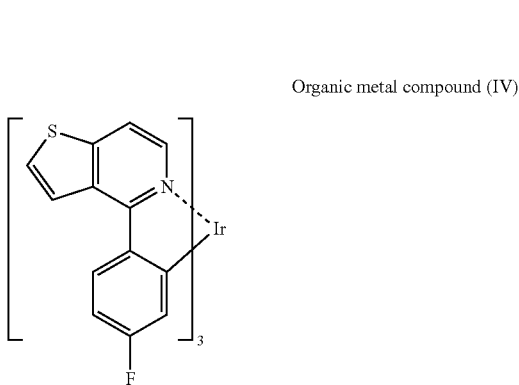

30.0 g f 2-(2-aminoethyl)thiophene (235.8 mmol), and 400 mL of water were added into a reaction bottle. Next, 40.9 g of 4-fluorine-benzoyl chloride (259.4 mmol) and sodium hydroxide aqueous solution (20 wt %, 200 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (16) with a yield of 93%. The synthesis pathway of the above reaction was as follows:

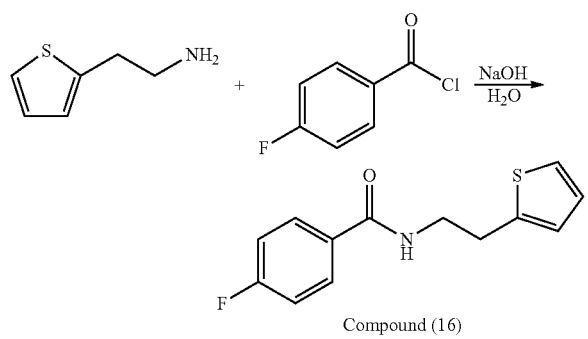

Compound (16)

5.0 g of Compound (16) (20.1 mmol) and 100 mL of toluene were added into a reaction bottle, and the reaction bottle was cooled to 0° C. Next, 9.2 g of phosphoryl chloride ($POCl_3$, 60.21 mmol) was added slowly into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (17) with a yield of 55%. The synthesis pathway of the above reaction was as follows:

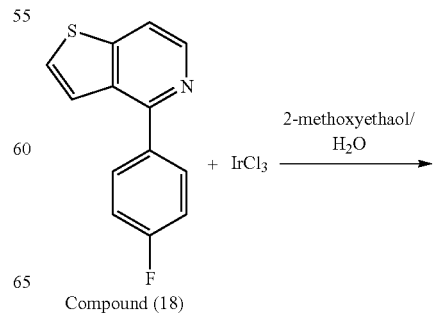

Compound (16)

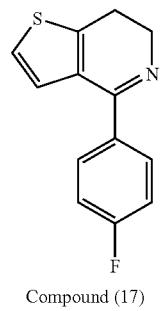

Compound (17)

5.0 g of Compound (17) (21.6 mmol), 5 g of Pd/C catalyst (palladium 10% on carbon), and 30 mL of toluene were added into a reaction bottle. Next, the reaction bottle was heated to reflux. Next, after removing Pd/C catalyst by filtration, the filtrate was extracted three times using ethyl acetate and water. Next, an organic phase was separated and concentrated, and then purified by column chromatography, obtaining Compound (18) with a yield of 85%. The synthesis pathway of the above reaction was as follows:

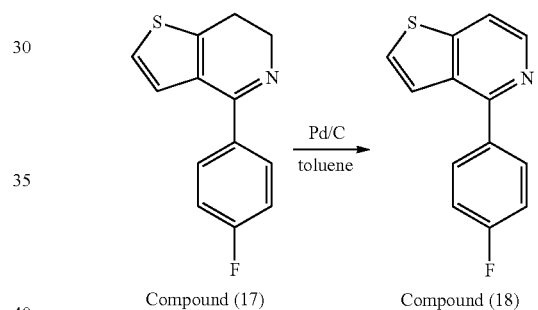

Compound (17)         Compound (18)

Next, 1.69 g of Compound (18) (7.4 mmol), and 1000 mg of $IrCl_3$ (3.35 mmol), 30 mL of 2-methoxyethanol, and 10 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (19) with a yield of 70%. The synthesis pathway of the above reaction was as follows:

Compound (18)

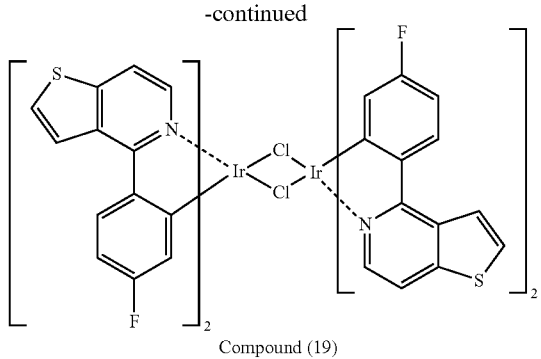

Compound (19)

Next, 3.0 g of Compound (19) (2.2 mmol), 880 mg of acetyl acetone (8.8 mmol), 930 mg of sodium carbonate (Na$_2$CO$_3$, 8.8 mmol), and 20 mL of 2-methoxyethanol were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (20) with a yield of 75%. The synthesis pathway of the above reaction was as follows:

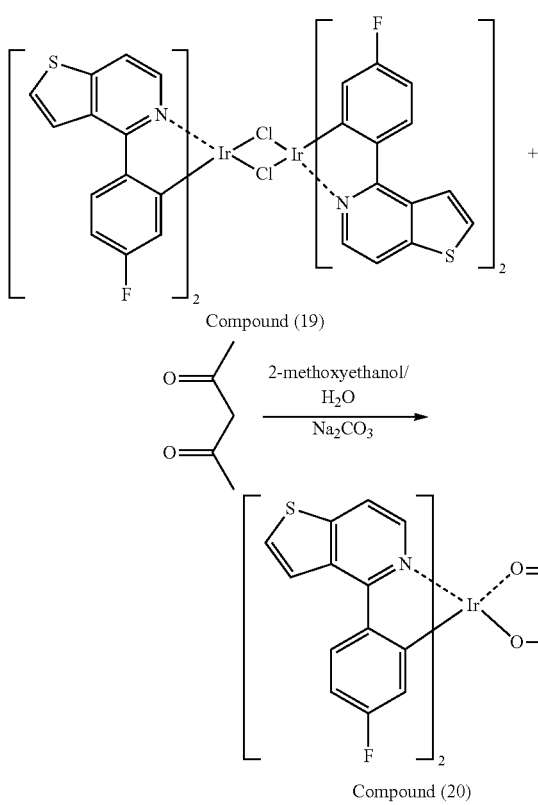

1000 mg of Compound (20) (1.33 mmol), 610 mg of Compound (18) (2.7 mmol), and 20 mL of glycerol were added into a reaction bottle. Next, after removing moisture and purging nitrogen gas several times, the reaction bottle was heated to 200° C. After reacting for 48 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (IV). The synthesis pathway of the above reaction was as follows:

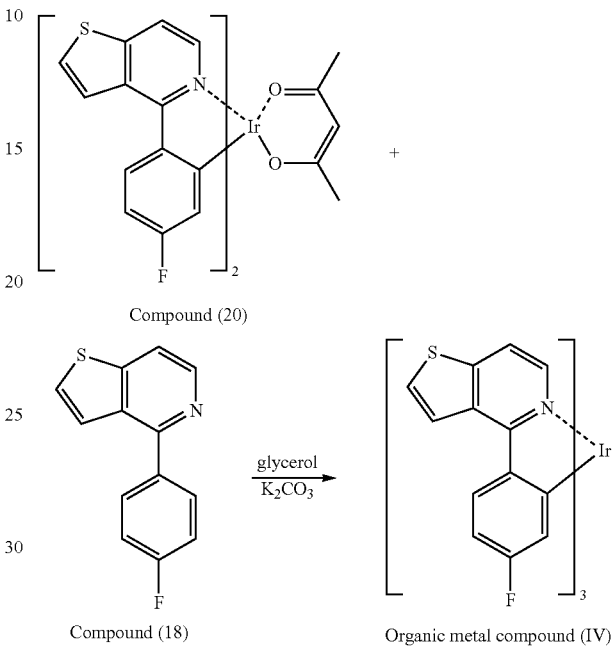

Example 5: Preparation of Organic Metal Compound (V)

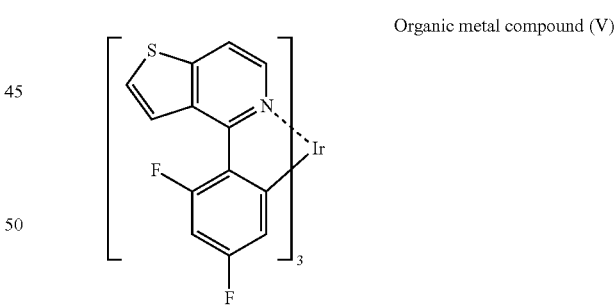

30.0 g of 2-(2-aminoethyl)thiophene (235.8 mmol), and 500 mL of water were added into a reaction bottle. Next, 45.6 g of 2,4-difluorine-benzoyl chloride (259.4 mmol) and sodium hydroxide aqueous solution (20 wt %, 200 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (21) with a yield of 90%. The synthesis pathway of the above reaction was as follows:

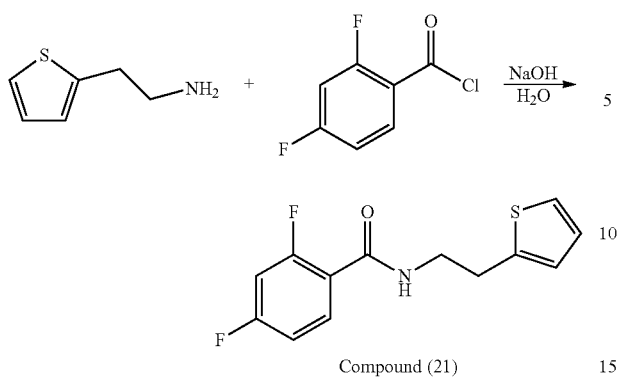

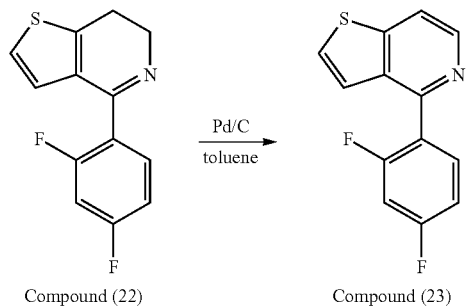 [SMILES: Fc1ccc(C2=NCCc3sccc32)c(F)c1 ; Fc1ccc(-c2nccc3sccc23)c(F)c1]

Compound (22)    Compound (23)

Next, compound (23) (1000 mg, 4.0 mmol), and IrCl$_3$ (548 mg, 1.84 mmol), 2-methoxyethanol, 30 mL), and 10 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (24) with a yield of 78%. The synthesis pathway of the above reaction was as follows:

5.0 g of compound (21) (18.7 mmol) and 100 mL of toluene were added into a reaction bottle, and the reaction bottle was cooled to 0° C. Next, 8.5 g of phosphoryl chloride (POCl$_3$, 56.2 mmol) was added slowly into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (22) with a yield of 53%. The synthesis pathway of the above reaction was as follows:

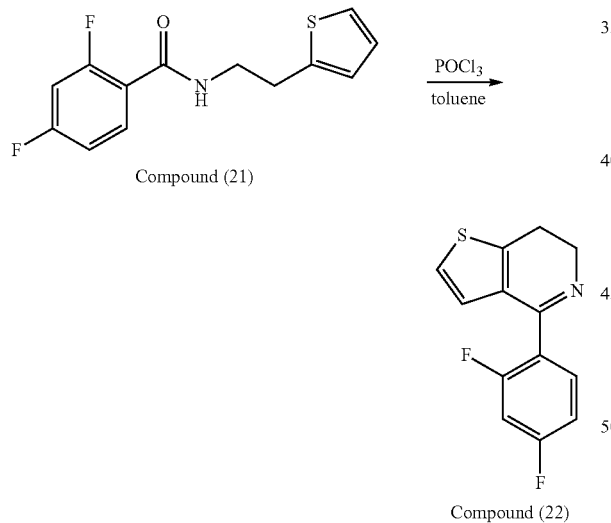

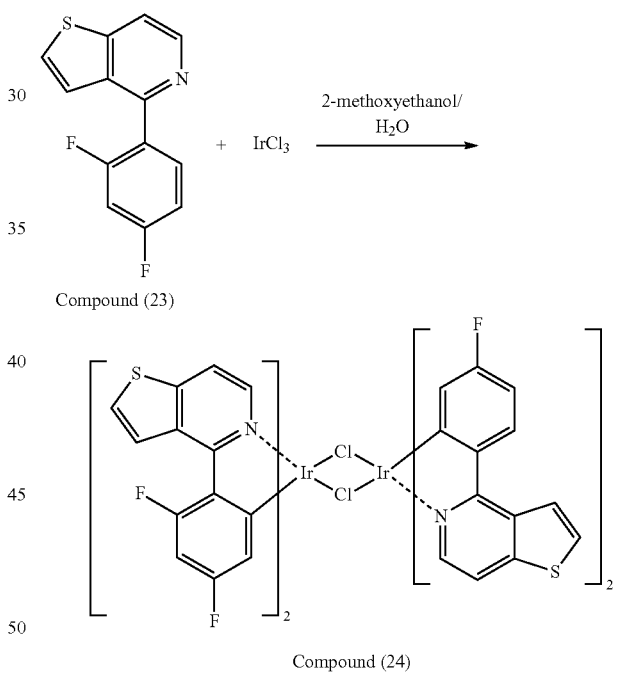

5.0 g of Compound (22) (20.1 mmol), 5.0 g of Pd/C catalyst (palladium 10% on carbon), and 30 mL of toluene were added into a reaction bottle. Next, the reaction bottle was heated to reflux. Next, after removing Pd/C catalyst by filtration, the filtrate was extracted three times using ethyl acetate and water. Next, an organic phase was separated and concentrated, and then purified by column chromatography, obtaining Compound (23) with a yield of 85%. The synthesis pathway of the above reaction was as follows:

Next, Compound (24) (1.04 g, 0.72 mmol), 289 mg of acetyl acetone (2.9 mmol), 306 mg of sodium carbonate (Na$_2$CO$_3$, 2.9 mmol), and 30 mL of 2-methoxyethanol were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (25) with a yield of 70%. The synthesis pathway of the above reaction was as follows:

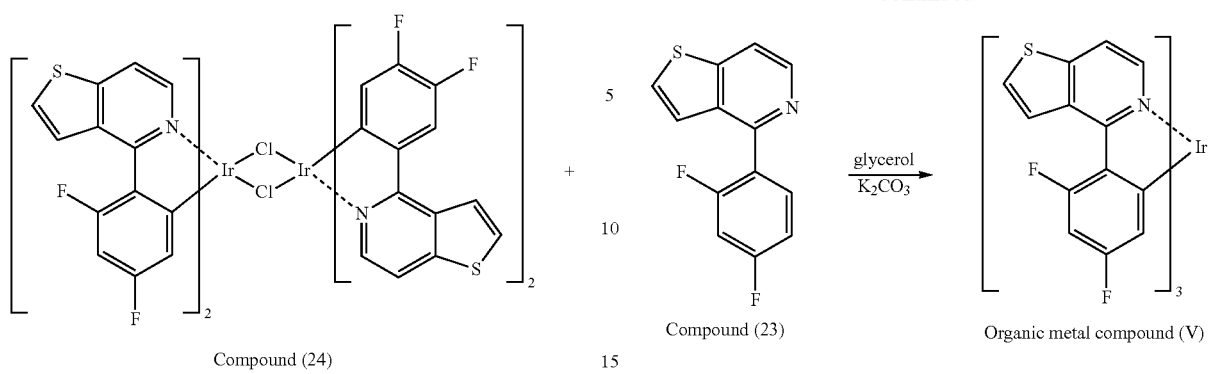

Compound (24)

Compound (25)

782 mg of Compound (25) (0.99 mmol), 492 mg of Compound (23) (1.99 mmol), and 15 mL of glycerol were added into a reaction bottle. Next, after removing moisture and purging nitrogen gas several times, the reaction bottle was heated to 200° C. After reacting for 96 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (V). The synthesis pathway of the above reaction was as follows:

Compound (25)

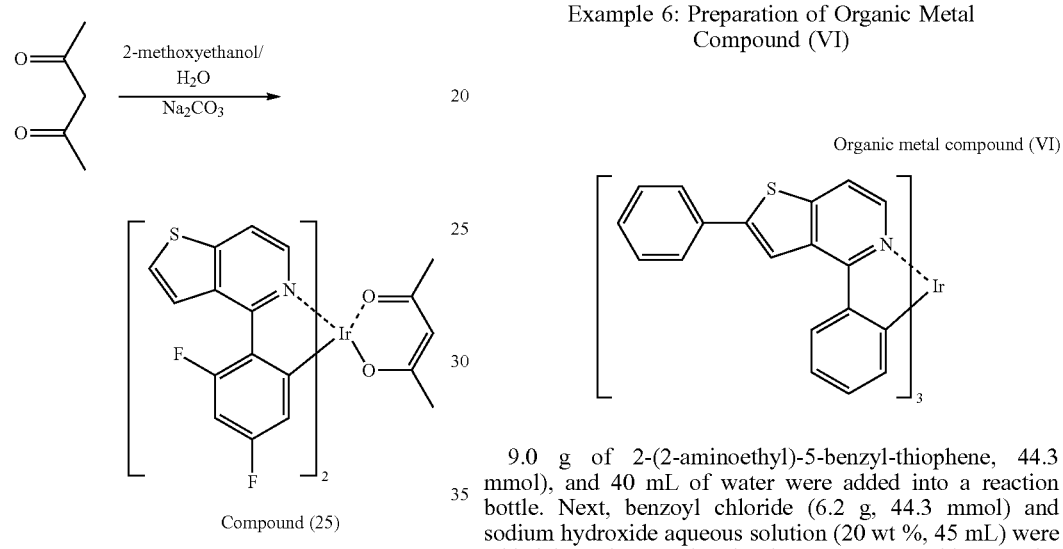

Compound (23)

Organic metal compound (V)

Example 6: Preparation of Organic Metal Compound (VI)

Organic metal compound (VI)

9.0 g of 2-(2-aminoethyl)-5-benzyl-thiophene, 44.3 mmol), and 40 mL of water were added into a reaction bottle. Next, benzoyl chloride (6.2 g, 44.3 mmol) and sodium hydroxide aqueous solution (20 wt %, 45 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (26) with a yield of 91%. The synthesis pathway of the above reaction was as follows:

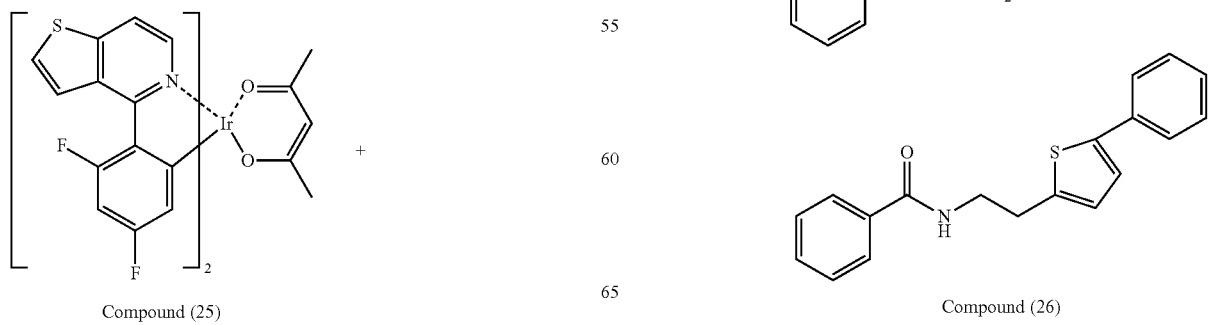

Compound (26)

15.4 g of Compound (26) (50 mmol) and 50 mL of toluene were added into a reaction bottle, and the reaction bottle was cooled to 0° C. Next, 11.5 g of phosphoryl chloride (POCl$_3$, 75 mmol) was slowly added into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (27) with a yield of 71%. The synthesis pathway of the above reaction was as follows:

14.5 g of Compound (27) (50 mmol), 10 g of Pd/C catalyst (palladium 10% on carbon), and 50 mL of toluene were added into a reaction bottle. Next, the reaction bottle was heated to reflux. Next, after removing Pd/C catalyst by filtration, the filtrate was extracted three times using ethyl acetate and water. Next, an organic phase was separated and concentrated, and then purified by column chromatography, obtaining Compound (28) with a yield of 94%. The synthesis pathway of the above reaction was as follows:

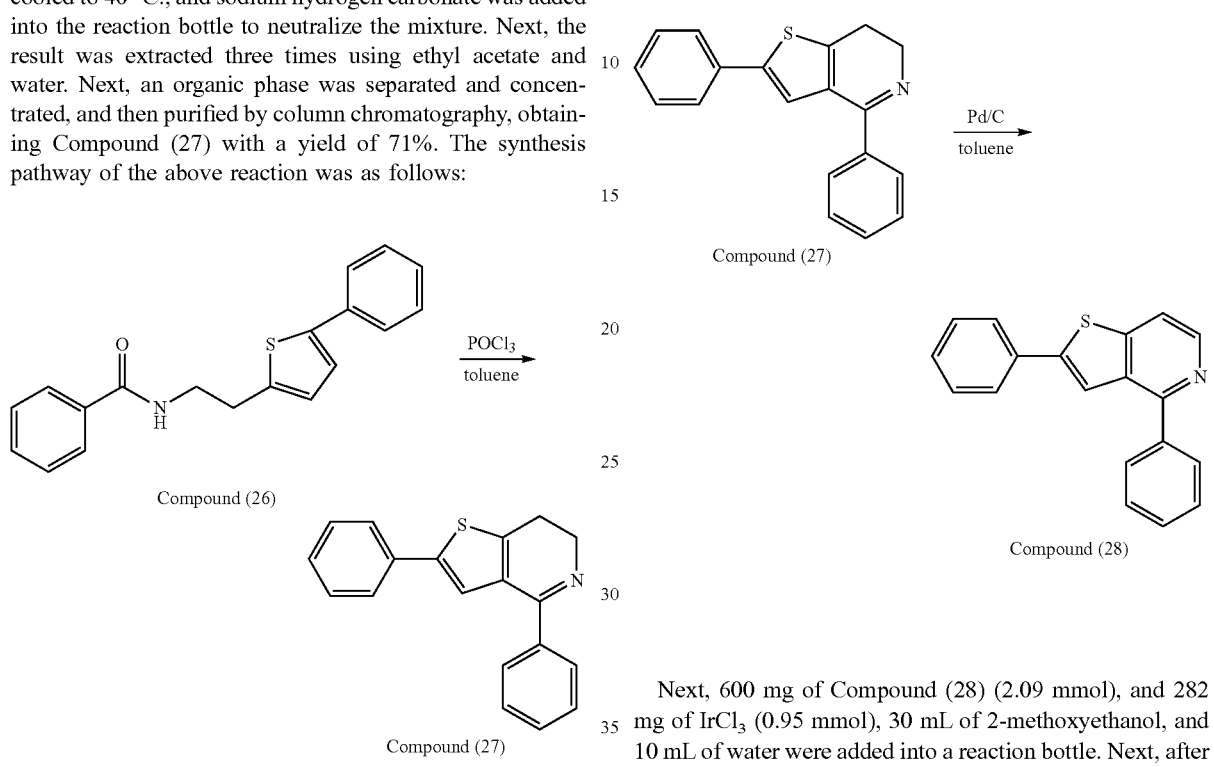

Next, 600 mg of Compound (28) (2.09 mmol), and 282 mg of IrCl$_3$ (0.95 mmol), 30 mL of 2-methoxyethanol, and 10 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (29) with a yield of 65%. The synthesis pathway of the above reaction was as follows:

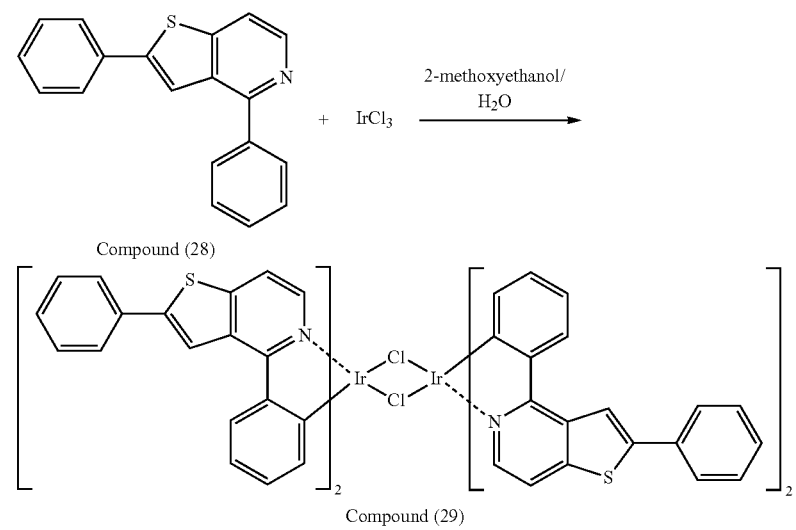

Next, 595 mg of compound (29) (0.37 mmol), 148 mg of acetyl acetone (1.47 mmol), sodium carbonate 157 mg of (Na$_2$CO$_3$, 1.48 mmol), and 2-methoxyethanol, 30 mL) were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining compound (30) with a yield of 65%. The synthesis pathway of the above reaction was as follows:

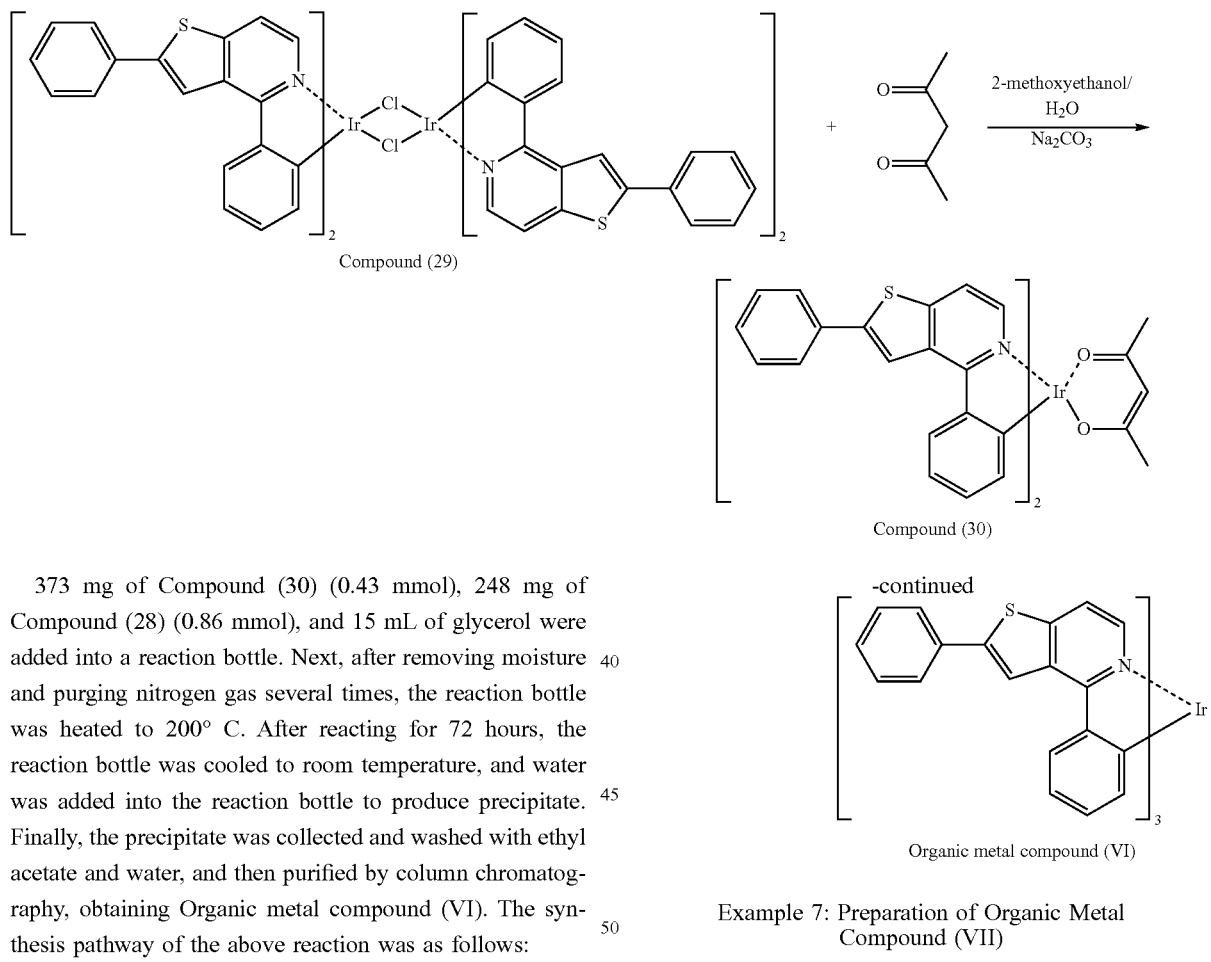

373 mg of Compound (30) (0.43 mmol), 248 mg of Compound (28) (0.86 mmol), and 15 mL of glycerol were added into a reaction bottle. Next, after removing moisture and purging nitrogen gas several times, the reaction bottle was heated to 200° C. After reacting for 72 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (VI). The synthesis pathway of the above reaction was as follows:

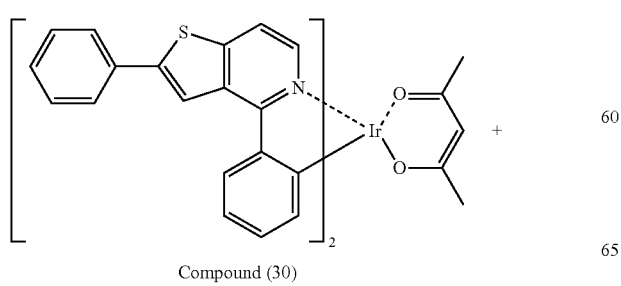

Compound (30)

Example 7: Preparation of Organic Metal Compound (VII)

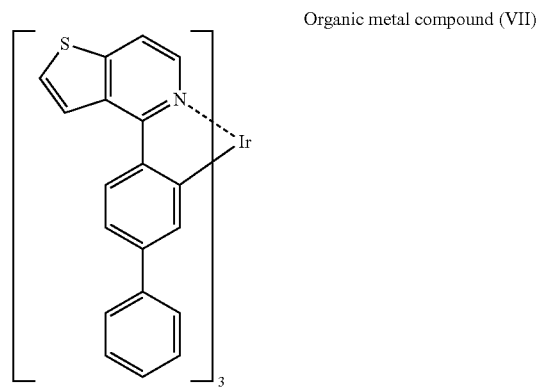

Organic metal compound (VII)

10.0 g of 2-(2-aminoethyl)thiophene (78.7 mmol) and 100 mL of water were added into a reaction bottle. Next, 17 g of 4-benzyl-benzoyl chloride (78.7 mmol) and sodium hydroxide aqueous solution (20 wt %, 50 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (31) with a yield of 82%. The synthesis pathway of the above reaction was as follows:

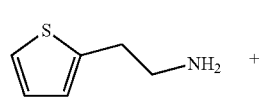  +

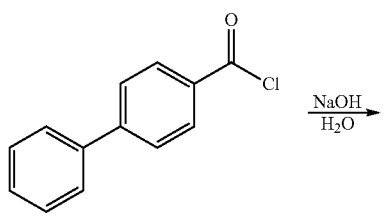

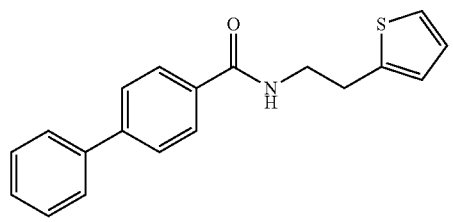

Compound (31)

5.0 g of compound (31) (16.3 mmol) and 100 mL of toluene were added into a reaction bottle, and the reaction bottle was cooled to 0° C. Next, 7.4 g of phosphoryl chloride (POCl₃, 48.8 mmol) was added slowly into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (32) with a yield of 55%. The synthesis pathway of the above reaction was as follows:

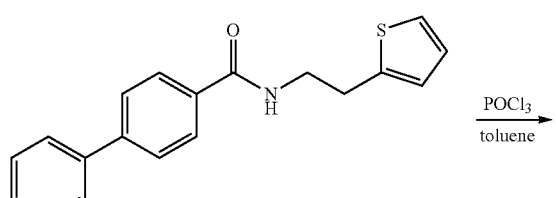

Compound (31)

-continued

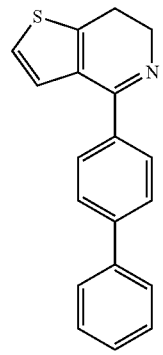

Compound (32)

5.0 g of Compound (32) (17.3 mmol), 5.0 g of Pd/C catalyst (palladium 10% on carbon), and 30 mL of toluene were added into a reaction bottle. Next, the reaction bottle was heated to reflux for 24 hours. Next, after removing Pd/C catalyst by filtration, the filtrate was extracted three times using ethyl acetate and water. Next, an organic phase was separated and concentrated, and then purified by column chromatography, obtaining Compound (33) with a yield of 80%. The synthesis pathway of the above reaction was as follows:

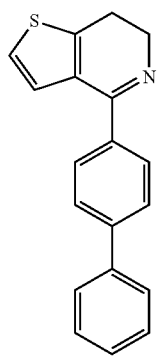 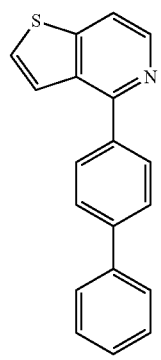

Compound (32)    Compound (33)

Next, 5.0 g of compound (33) (17.4 mmol), and 2360 mg of IrCl₃ (7.9 mmol), 50 mL of 2-methoxyethanol, and 17 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (34) with a yield of 65%. The synthesis pathway of the above reaction was as follows:

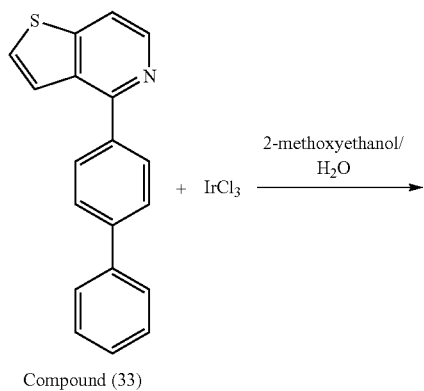

Compound (33)

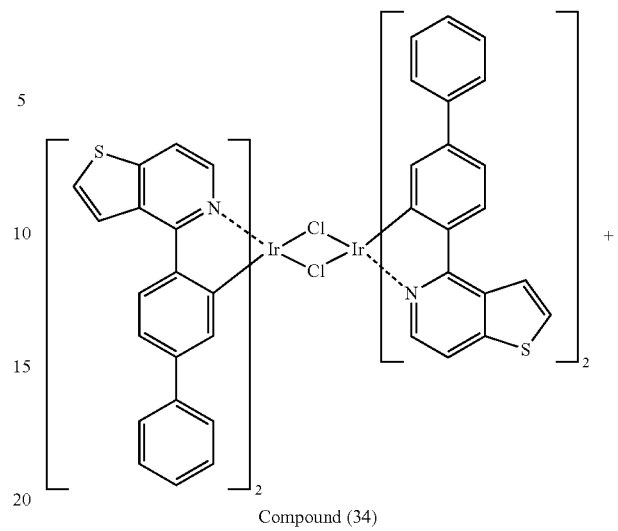

Compound (34)

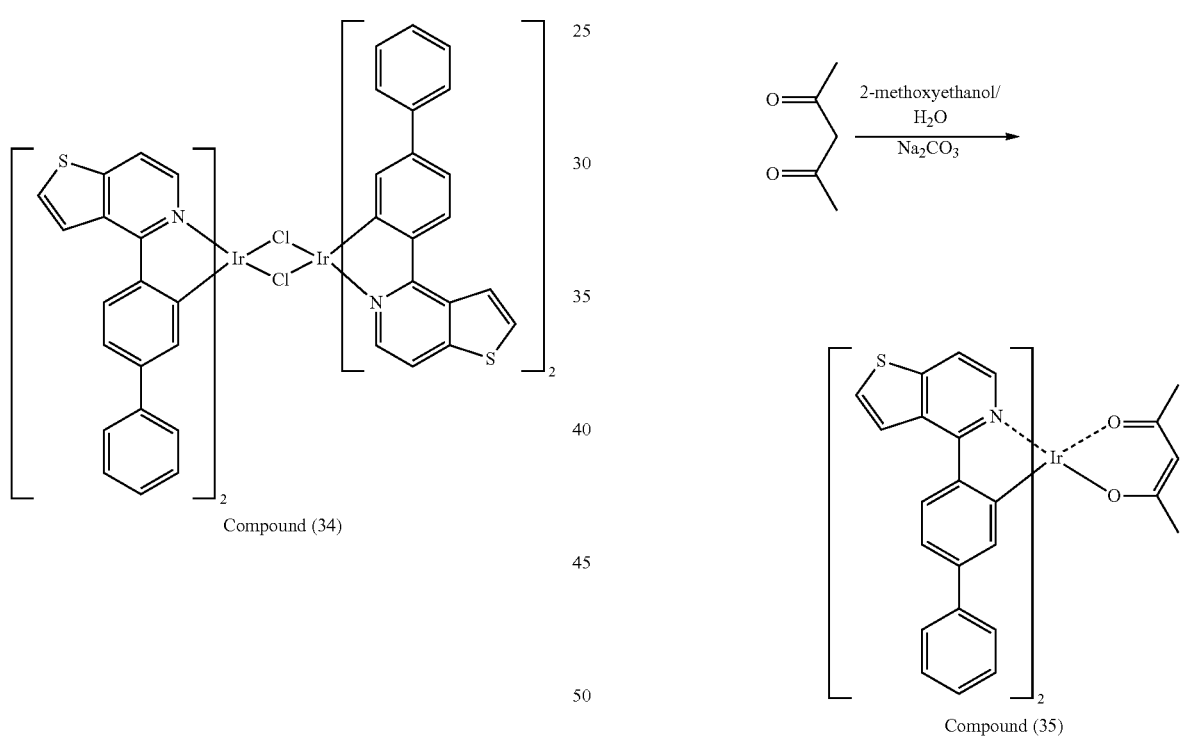

Compound (34)

Compound (35)

Next, 3.0 g of Compound (34) (1.87 mmol), 750 mg of acetyl acetone (7.5 mmol), 790 mg of sodium carbonate ($Na_2CO_3$, 7.5 mmol), and 30 mL of 2-methoxyethanol were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (35) with a yield of 68%. The synthesis pathway of the above reaction was as follows:

1000 mg of Compound (35) (1.16 mmol), 660 mg of Compound (33) (2.3 mmol), and 25 mL of glycerol were added into a reaction bottle. Next, after removing moisture and purging nitrogen gas several times, the reaction bottle was heated to 200° C. After reacting for 72 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (VII). The synthesis pathway of the above reaction was as follows:

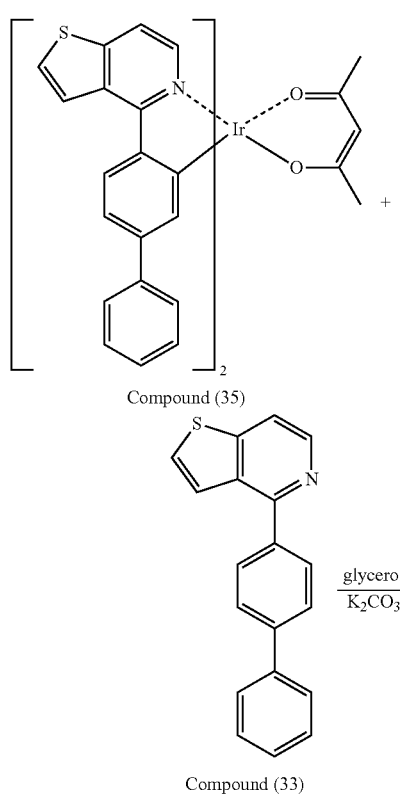

Compound (35)

Compound (33)

Organic metal compound (VII)

Example 8: Preparation of Organic Metal Compound (VIII)

Organic metal compound (VIII)

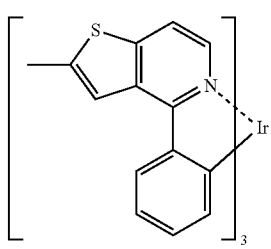

9.0 g of 2-(2-aminoethyl)-5-methyl-thiophene (63.7 mmol) and 40 mL of water were added into a reaction bottle. Next, 8.9 g of benzoyl chloride (63.7 mmol) and sodium hydroxide aqueous solution (20 wt %, 45 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (36) with a yield of 90%. The synthesis pathway of the above reaction was as follows:

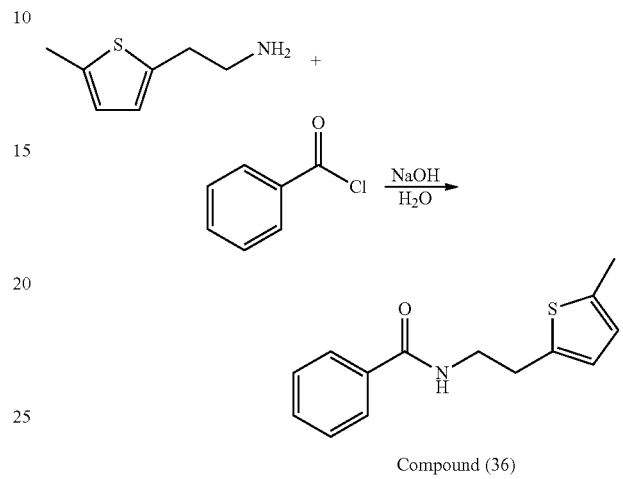

Compound (36)

5.0 g of Compound (36) (20.4 mmol) and 30 mL of toluene were added into a reaction bottle, and the reaction bottle was cooled to 0° C. Next, 4.7 g of phosphoryl chloride (POCl$_3$, 30.6 mmol) was added slowly into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining Compound (37) with a yield of 70%. The synthesis pathway of the above reaction was as follows:

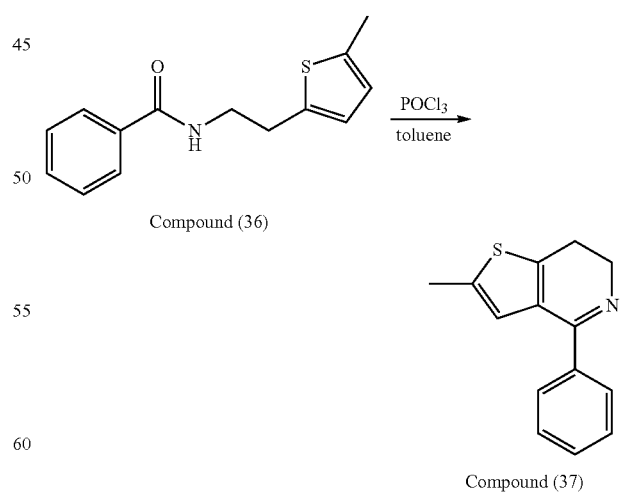

Compound (37)

11.4 g of Compound (37) (50 mmol), 10 g of Pd/C catalyst (palladium 10% on carbon), and 50 mL of toluene were added into a reaction bottle. Next, the reaction bottle was heated to reflux for 12 hours. Next, after removing Pd/C catalyst by filtration, the filtrate was extracted three times using ethyl acetate and water. Next, an organic phase was separated and concentrated, and then purified by column chromatography, obtaining Compound (38) with a yield of 92%. The synthesis pathway of the above reaction was as follows:

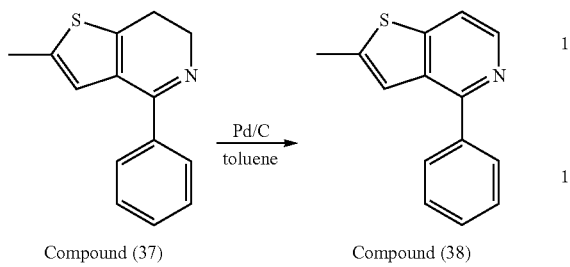

Next, 991 mg of Compound (38) (4.4 mmol), and 598 mg of IrCl₃ (2 mmol), 15 mL of 2-methoxyethanol, and 5 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (39) with a yield of 69%. The synthesis pathway of the above reaction was as follows:

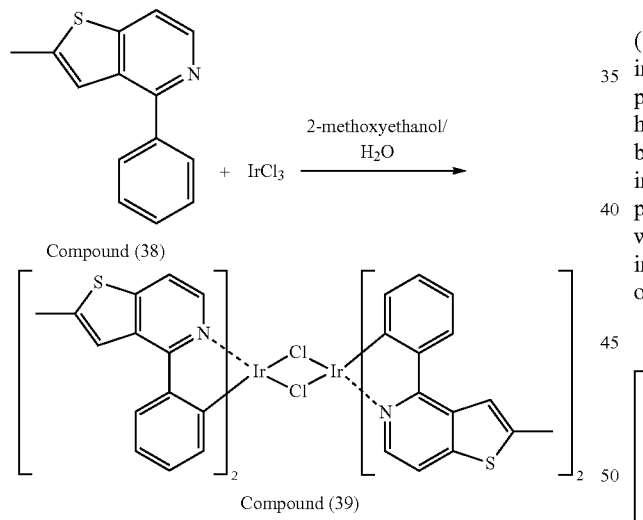

Next, 1.3 g of Compound (39) (1 mmol), 300 mg of acetyl acetone (3 mmol), 212 mg of sodium carbonate (Na₂CO₃, 2 mmol), and 20 mL of 2-methoxyethanol were added into a reaction bottle. Next, After removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (40) with a yield of 75%. The synthesis pathway of the above reaction was as follows:

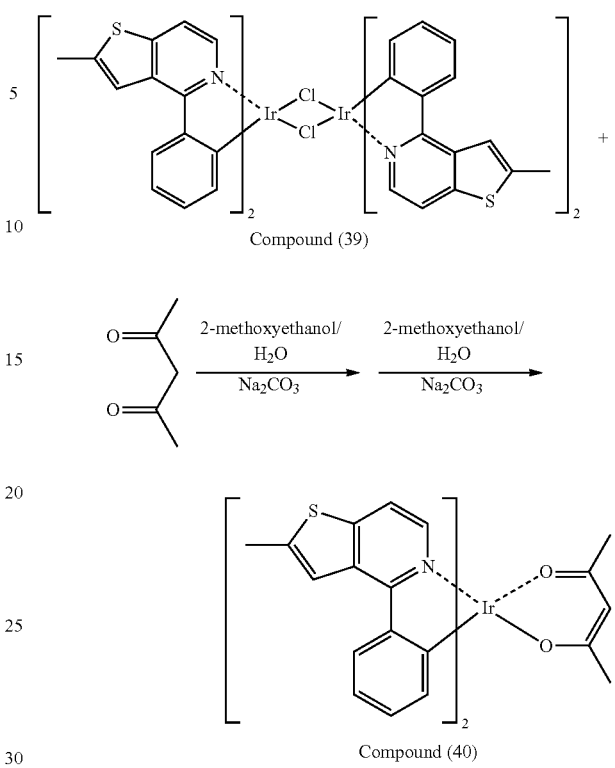

3000 mg Compound (40) (4.05 mmol), compound (38) (1820 mg, 8.1 mmol), and 15 mL of glycerol were added into a reaction bottle. Next, After removing moisture and purging nitrogen gas several times, the reaction bottle was heated to 200° C. After reacting for 48 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (VIII). The synthesis pathway of the above reaction was as follows:

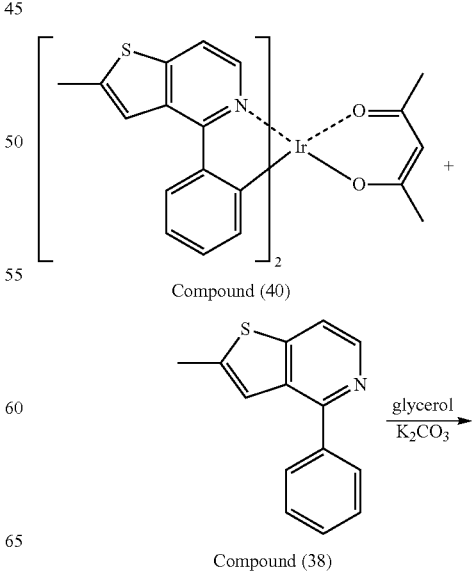

-continued

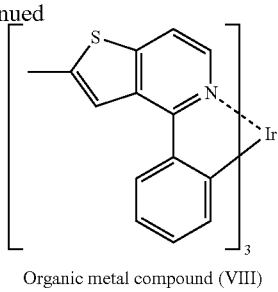

Organic metal compound (VIII)

Example 9: Preparation of Organic Metal Compound (IX)

Organic metal compound (IX)

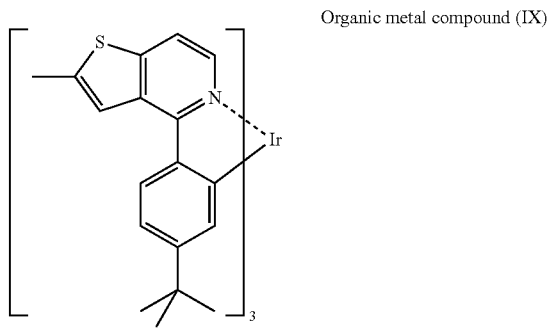

9.0 g of 2-(2-aminoethyl)-5-methyl-thiophene (63.7 mmol) and 40 mL of water were added into a reaction bottle. Next, 12.5 g of 4-tert-butylbenzoyl chloride (63.7 mmol) and sodium hydroxide aqueous solution (20 wt %, 45 mL) were added into the reaction bottle at 0° C. A white powder product was separated out during the reaction. Next, after reacting for 12 hours, the mixture was filtrated and the filter cake was collected. Next, the filter cake was ground to fine powders and washed with water and hexane, obtaining Compound (41) with a yield of 85%. The synthesis pathway of the above reaction was as follows:

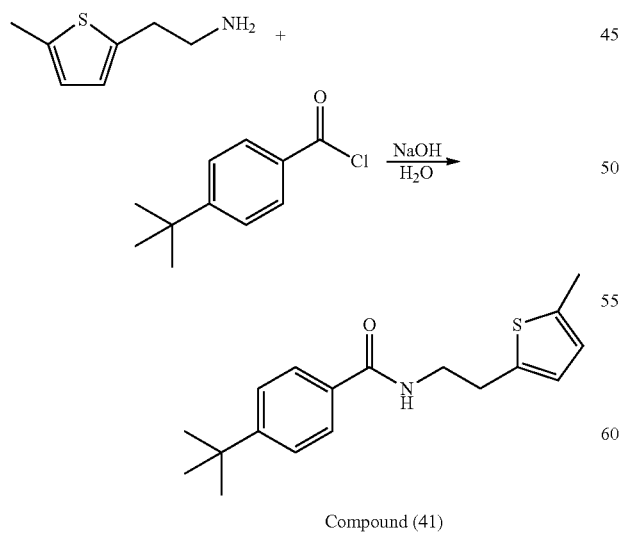

15.1 g of Compound (41) (50 mmol) and 50 mL of toluene were added into a reaction bottle, and the reaction bottle was cooled to 0° C. Next, 11.5 g of phosphoryl chloride (POCl$_3$, 75 mmol) was slowly added into the reaction bottle. After the addition was complete, the reaction bottle was heated to reflux. After reacting for 2 hours, the reaction bottle was cooled to 40° C., and sodium hydrogen carbonate was added into the reaction bottle to neutralize the mixture. Next, the result was extracted three times using ethyl acetate and water. Next, an organic phase was separated and concentrated, and then purified by column chromatography, obtaining compound (42) with a yield of 74%. The synthesis pathway of the above reaction was as follows:

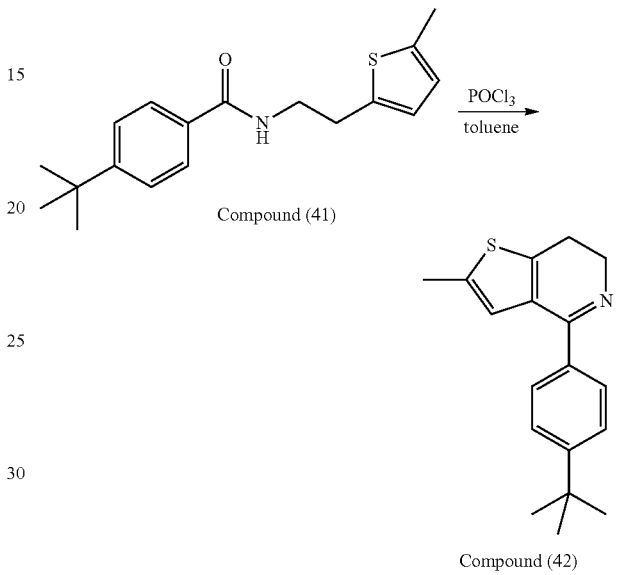

14.2 g of Compound (42) (50 mmol), 10 g of Pd/C catalyst (palladium 10% on carbon), and 50 mL of toluene were added into a reaction bottle. Next, the reaction bottle was heated to reflux. Next, after removing Pd/C catalyst by filtration, the filtrate was extracted three times using ethyl acetate and water. Next, an organic phase was separated and concentrated, and then purified by column chromatography, obtaining Compound (43) with a yield of 91%. The synthesis pathway of the above reaction was as follows:

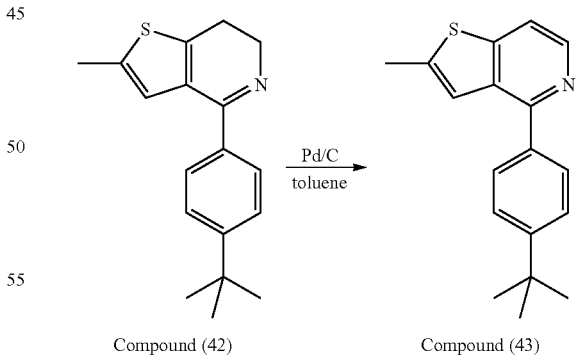

Next, 1238 mg of Compound (43) (4.4 mmol), and 598 mg of IrCl$_3$ (2 mmol), 2-methoxyethanol, 15 mL), and 5 mL of water were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dried under vacuum, obtaining Compound (44) with a yield of 76%. The synthesis pathway of the above reaction was as follows:

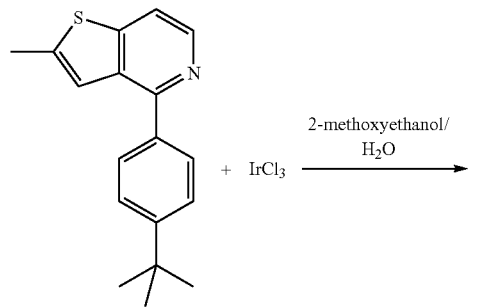

Compound (43)

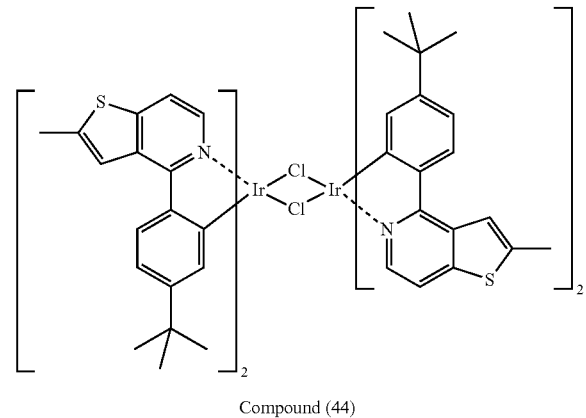

Compound (44)

Next, 1.57 g of Compound (44) (1 mmol), 300 mg acetyl acetone (3 mmol), 212 mg of sodium carbonate (Na$_2$CO$_3$, 2 mmol), and 2-methoxyethanol, 20 mL) were added into a reaction bottle. Next, after removing moisture and purging nitrogen gas several times, the reaction bottle was heated to 120° C. After reacting for 12 hours and cooling down to room temperature, the result was filtrated. The filter cake was collected and washed with water and hexane, and then dissolved in dichloromethane. Next, the solution was extracted three times using dichloromethane and water. Next, an organic phase was separated and concentrated, and then purified by column chromatography, obtaining Compound (45) with a yield of 71%. The synthesis pathway of the above reaction was as follows:

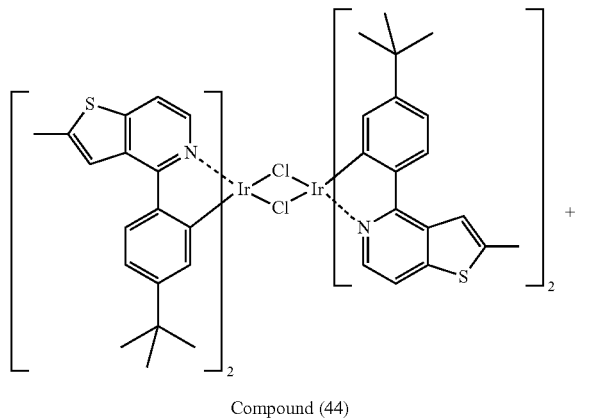

Compound (44)

-continued

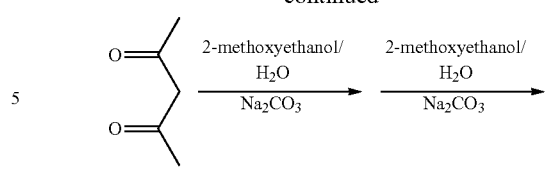

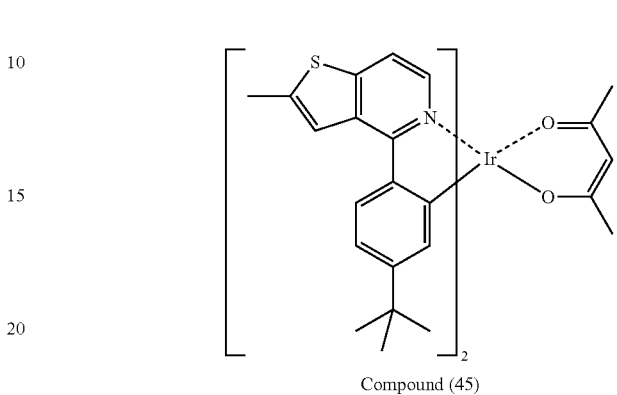

Compound (45)

852 mg of Compound (45) (1 mmol), 562 mg of Compound (43) (2 mmol), and 5 mL of glycerol were added into a reaction bottle. Next, after removing moisture and purging nitrogen gas several times, the reaction bottle was heated to 200° C. After reacting for 48 hours, the reaction bottle was cooled to room temperature, and water was added into the reaction bottle to produce precipitate. Finally, the precipitate was collected and washed with ethyl acetate and water, and then purified by column chromatography, obtaining Organic metal compound (IX). The synthesis pathway of the above reaction was as follows:

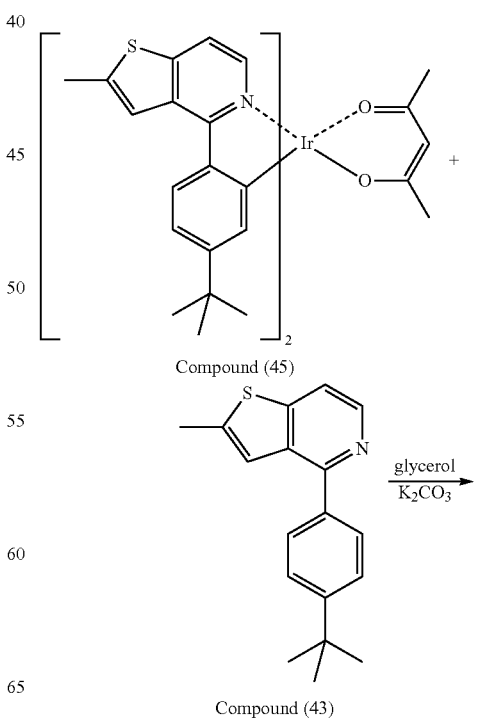

Compound (45)

Compound (43)

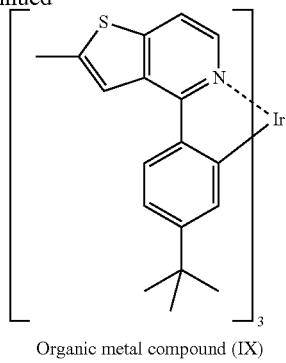

Organic metal compound (IX)

Next, thermal degradation temperature ($T_d$) of Organic metal compounds (I)-(V) was measured by thermogravimetric analyzer (TGA), and the result is shown in Table 1. Next, Organic metal compounds (I)-(V) were dissolved into $CH_2Cl_2$ individually obtaining solutions with a concentration of $10^{-5}$ M. Next, the photoluminescence (PL) spectra and the maximum luminous intensity peak (Emission $\lambda_{max}$) of the solutions were measured, and the results are shown in Table 1.

TABLE 1

|  | thermal degradation temperature ($T_d$, °C.) | maximum luminous intensity peak (Emission $\lambda_{max}$, nm) |
| --- | --- | --- |
| Organic metal compound (I) | 421 | 560 |
| Organic metal compound (II) | 444 | 556 |
| Organic metal compound (III) | 413 | 552 |
| Organic metal compound (IV) | 435 | 528 |
| Organic metal compound (V) | 403 | 534 |

As shown in Table 1, the organic metal compound of the disclosure can have a thermal degradation temperature ($T_d$) that is higher than 400° C. Therefore, the organic metal compound is suitable for being purified by a sublimation process. In addition, Organic metal compound (I) (with 4-phenylthieno[3,2-c]pyridine ligand) has a maximum luminous intensity peak of 560 nm, and can serve as a yellow phosphorescent material. Furthermore, the organic metal compounds with a modified 4-phenylthieno[3,2-c]pyridine ligand, which the hydrogen bonded in the phenyl group thereof is replaced with an electron withdrawing group (such as fluorine), can exhibit a blue-shifted emission in comparison with Organic metal compound (I). For example, Organic metal compounds (IV) and (V) have a maximum luminous intensity peak of 528 nm and 534 nm respectively, and can serve as green phosphorescent materials.

Organic Light-Emitting Device

Figure 2:
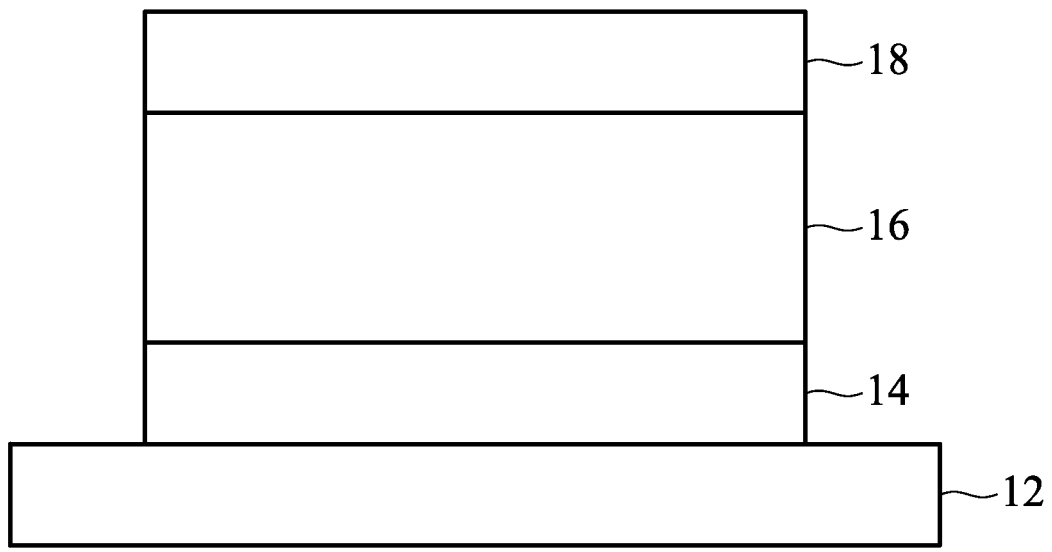
FIG. 2 shows a cross section of an organic light-emitting device disclosed by an embodiment of the disclosure.

FIG. 2 shows an embodiment of an organic light-emitting device 10. The organic light-emitting device 10 includes a substrate 12, a bottom electrode 14, an organic light-emitting element 16, and a top electrode 18, as shown in FIG. 2. The organic light-emitting device 10 can be a top-emission, bottom-emission, or dual-emission devices. The substrate 12 can be a glass, plastic, or semiconductor substrate. Suitable materials for the bottom electrode 14 and top electrode 18 can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Furthermore, at least one of the bottom and top electrodes 14 and 18 is transparent.

The organic light-emitting element 16 at least includes an emission layer, and can further include a hole injection layer, a hole transport layer, an electron transport layer, and an electron injection layer. In an embodiment of the disclosure, at least one layer of the organic light-emitting element 16 includes the aforementioned organometallic compound.

According to another embodiment of the disclosure, the organic light-emitting device can be a phosphorescent organic light-emitting device, and the emission layer of the organic light-emitting element can include a host material and a dopant, wherein the dopant can include the aforementioned organic compounds. The dose of the dopant is not limited and can optionally be modified by a person of ordinary skill in the field.

In order to clearly disclose the organic light-emitting devices of the disclosure, the following examples (having an emitting layer employing the organic metal compounds of the disclosure formed by deposition (dry process) or coating (wet process)) are intended to illustrate the disclosure more fully without limiting their scope, since numerous modifications and variations will be apparent to those skilled in this art.

Example 10: Organic Light-Emitting Device (I)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

Next, PEDOT(poly(3,4)-ethylendioxythiophen):PSS(e-polystyrenesulfonate) was coated on the ITO film by a blade and spin coating process (with a rotation rate of 4000 rpm) and baked at 100° C. for 40 min to form a PEDOT:PSS film serving as a hole injection layer (with a thickness of 50 nm). Next, TAPC (1,1-bis[4-[N,N'-di(p-tolyl)amino]phenyl]cyclohexane, with a thickness of 40 nm), TCTA (4,4',4'-tri(N-carbazolyl)triphenylamine) doped with Organic metal compound (I) (the weight ratio between TCTA and Organic metal compound (I) was 100:6, with a thickness of 10 nm), TmPyPB (1,3,5-tri(p-pyrid-3-yl-phenyl)benzene, with a thickness of 42 nm), LiF (with a thickness of 0.5 nm), and Al (with a thickness of 120 nm), were subsequently formed on the PEDOT:PSS film at $10^{-6}$ torr, obtaining the organic light-emitting device (I) after encapsulation. The materials and layers formed therefrom are described in the following: ITO/PEDOT/TAPC/TCTA:Organic metal compound (I) (6%)/TmPyPB/LiF/Al Next, the optical properties of the light-emitting device (I) were measured by a spectra colorimeter PR650 (purchased from Photo Research Inc.) and a luminance meter LS110 (purchased from Konica Minolta). The results are shown in Table 2.

Example 11: Organic Light-Emitting Device (II)

Example 11 was performed in the same manner as in Example 10 except that Organic metal compound (II) was substituted for Organic metal compound (I), obtaining the organic light-emitting device (II). The materials and layers formed therefrom are described in the following: ITO/ PEDOT/TAPC/TCTA:Organic metal compound (II) (6%)/ TmPyPB/LiF/Al Next, the optical properties of the light-emitting device (II) were measured by a spectra colorimeter PR650 (purchased from Photo Research Inc.) and a luminance meter LS110 (purchased from Konica Minolta). The results are shown in Table 2.

Example 12: Organic Light-Emitting Device (III)

Example 12 was performed in the same manner as in Example 11 except that $Cs_2CO_3$ was substituted for LiF, obtaining the organic light-emitting device (III). The materials and layers formed therefrom are described in the following: ITO/PEDOT/TAPC/TCTA:organic metal compound (II) (6%)/TmPyPB/$Cs_2CO_3$/Al Next, the optical properties of the light-emitting device (III) were measured by a spectra colorimeter PR650 (purchased from Photo Research Inc.) and a luminance meter LS110 (purchased from Konica Minolta). The results are shown in Table 2.

Example 13: Organic Light-Emitting Device (IV)

Example 13 was performed in the same manner as in Example 10 except that Organic metal compound (III) was substituted for Organic metal compound (I), obtaining the organic light-emitting device (IV). The materials and layers formed therefrom are described in the following: ITO/ PEDOT/TAPC/TCTA:Organic metal compound (III) (6%)/ TmPyPB/LiF/Al Next, the optical properties of the light-emitting device (IV) were measured by a spectra colorimeter PR650 (purchased from Photo Research Inc.) and a luminance meter LS110 (purchased from Konica Minolta). The results are shown in Table 2.

Example 14: Organic Light-Emitting Device (V)

Example 14 was performed in the same manner as in Example 10 except that Organic metal compound (IV) was substituted for Organic metal compound (I), obtaining the organic light-emitting device (V). The materials and layers formed therefrom are described in the following: ITO/ PEDOT/TAPC/TCTA:Organic metal compound (IV) (6%)/ TmPyPB/LiF/Al Next, the optical properties of the light-emitting device (V) were measured by a spectra colorimeter PR650 (purchased from Photo Research Inc.) and a luminance meter LS110 (purchased from Konica Minolta). The results are shown in Table 2.

TABLE 2

|  | current efficiency (Cd/A) | power efficiency (lm/W) | maximum luminous intensity peak (nm) | C.I.E coordinate |
|---|---|---|---|---|
| organic light-emitting device (I) | 38.4 | 24.1 | 557 | (0.48, 0.51) |
| organic light-emitting device (II) | 74.6 | 46.9 | 556 | (0.48, 0.51) |
| organic light-emitting device (III) | 73.6 | 66.0 | 560 | (0.49, 0.51) |
| organic light-emitting device (IV) | 67.6 | 38.6 | 556 | (0.48, 0.52) |
| organic light-emitting device (V) | 48.8 | 30.7 | 528 | (0.38, 0.59) |

As shown in Table 2, the organic light-emitting devices (I)-(V) of the disclosure have a power efficiency that is equal to or greater than 24.1 lm/W (measured at a brightness of 1000 $Cd/m^2$). When Organic metal compounds (I)-(III) serve as a phosphorescence dopant material of the light-emitting layer, the obtained organic light-emitting devices are yellow organic light-emitting devices. In addition, when Organic metal compound (IV) serves as a phosphorescence dopant material of the light-emitting layer, the obtained organic light-emitting device is a green organic light-emitting device due to the blue-shifted emission resulting from the fluorine-modified 4-phenylthieno[3,2-c]pyridine ligand.

Moreover, since $Cs_2CO_3$ was substituted for LiF, the power efficiency of the organic light-emitting device (III) is about 1.41 times higher than that of the organic light-emitting device (II).

Example 15: Organic Light-Emitting Device (VI)

A glass substrate with an indium tin oxide (ITO) film with a thickness of 150 nm was provided and then washed with a cleaning agent, acetone, and isopropanol with ultrasonic agitation. After drying with nitrogen flow, the ITO film was subjected to a UV/ozone treatment for 30 min.

PEDOT(poly(3,4)-ethylendioxythiophen):PSS (e-polystyrenesulfonate) was coated on the ITO film by a blade and spin coating process (with a rotation rate of 4000 rpm) and baked at 100° C. for 40 min to form a PEDOT:PSS film serving as a hole injection layer (with a thickness of 50 nm). Next, a composition was used for forming a light-emitting layer coated on the PEDOT:PSS film by a blade coating process and baked at 100° C. for 40 min to form the light-emitting layer (with a thickness of 30 nm). The composition used for forming a light-emitting layer includes TCTA (4, 4',4'-tri(N-carbazolyl)triphenylamine) and Organic metal compound (II), wherein the weight ratio of TCTA and Organic metal compound (II) was 93:7, dissolved in chlorobenzene. Next, TmPyPB (1,3,5-tri(p-pyrid-3-yl-phenyl)benzene was coated on the light-emitting layer by a spin coating process to form a TmPyPB film (with a thickness of 50 nm). Next, LiF (with a thickness of 1 nm), and Al (with a thickness of 120 nm) were subsequently formed on the TmPyPB film at $10^{-6}$ torr, obtaining the organic light-emitting device (VI) after encapsulation. The materials and layers formed therefrom are described in the following: ITO/PEDOT/TCTA: Organic metal compound (II) (7%)/ TmPyPB/LiF/Al.

Next, the optical properties of the light-emitting device (VI) were measured by a spectra colorimeter PR650 (purchased from Photo Research Inc.) and a luminance meter LS110 (purchased from Konica Minolta).

During the formation of the light-emitting device (VI) via a wet process, it shows that Organic metal compound (II) exhibits high solubility when the solvent has a solid content that is greater than 4 wt %. Therefore, the organic metal compound of the disclosure can be uniformly mixed with the host material (TCTA). Furthermore, the organic light-emitting device (VI) fabricated via the wet process has a power efficiency of 13.5 lm/W (measured at a brightness of 1000 $Cd/m^2$).

While the disclosure has been described by way of example and in terms of the preferred embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organic metal compound, having a structure of Formula (I):

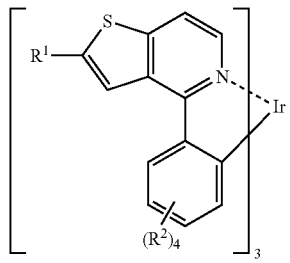

Formula (I)

wherein, $R^1$ is $C_{5-10}$ cycloalkyl group, $C_{3-12}$ heteroaryl group, or $C_{6-12}$ aryl group; $R^2$ is independently hydrogen, halogen, $C_{1-12}$ alkyl group, $C_{5-10}$ cycloalkyl group, $C_{3-12}$ heteroaryl group, or $C_{6-12}$ aryl group.

2. The organic metal compound as claimed in claim 1, wherein $R^1$ is cyclopentyl group, cyclohexyl group, phenyl group, biphenyl group, or naphthyl group.

3. The organic metal compound as claimed in claim 1, wherein $R^2$ is independently hydrogen, fluorine, methyl group, ethyl group, propyl group, isopropyl group, n-butyl group, isobutyl group, sec-butyl group, tert-butyl group, pentyl group, hexyl group, cyclopentyl group, cyclohexyl group, octyl group, decyl group, dodecyl group, phenyl group, biphenyl group, or naphthyl group.

4. The organic metal compound as claimed in claim 1, wherein the organic metal compound has a structure of Formula (II):

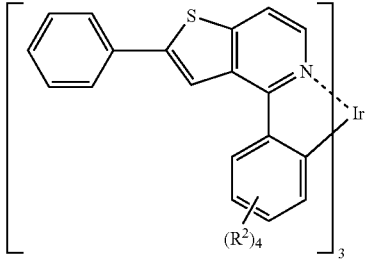

Formula (II)

wherein, $R^2$ is independently hydrogen, halogen, $C_{1-12}$ alkyl group, $C_{5-10}$ cycloalkyl group, $C_{3-12}$ heteroaryl group, or $C_{6-12}$ aryl group.

5. The organic metal compound as claimed in claim 4, wherein $R^2$ is independently hydrogen, fluorine, methyl group, ethyl group, propyl group, isopropyl group, n-butyl group, isobutyl group, sec-butyl group, tert-butyl group, pentyl group, hexyl group, cyclopentyl group, cyclohexyl group, octyl group, decyl group, dodecyl group, phenyl group, biphenyl group, or naphthyl group.

6. The organic metal compound as claimed in claim 4, wherein the organic metal compound is

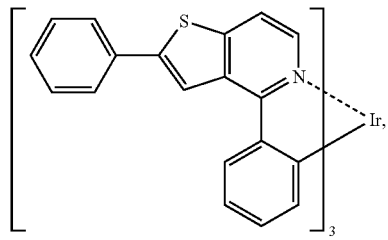

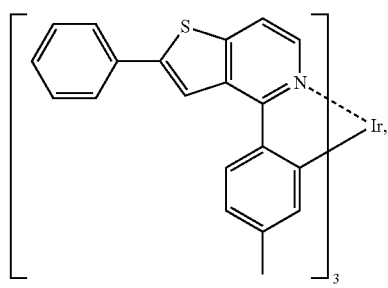

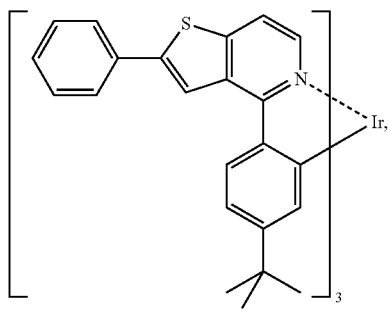

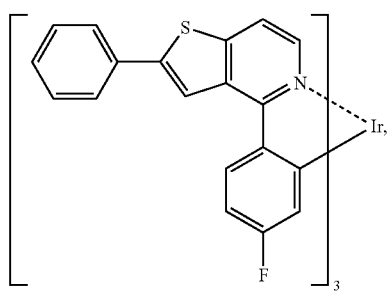

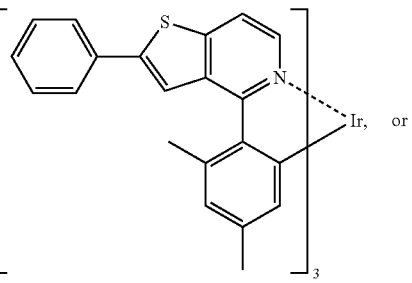

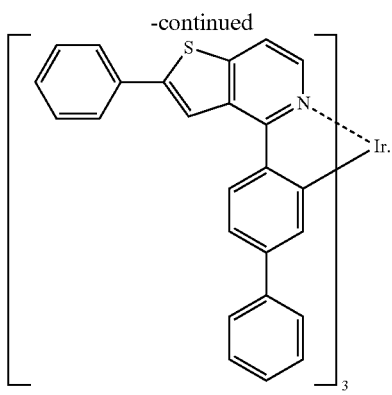

7. The organic metal compound as claimed in claim 1, wherein the organic metal compound has a structure of Formula (IV):

Formula (IV)

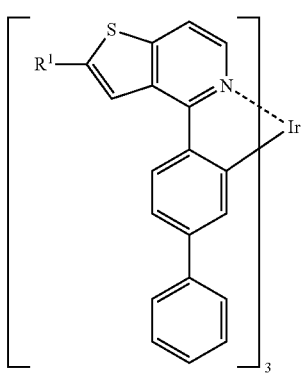

wherein, $R^1$ is $C_{5-10}$ cycloalkyl group, $C_{3-12}$ heteroaryl group, or $C_{6-12}$ aryl group.

8. The organic metal compound as claimed in claim 7, wherein $R^1$ is cyclopentyl group, cyclohexyl group, phenyl group, biphenyl group, or naphthyl group.

9. The organic metal compound as claimed in claim 1, wherein the organic metal compound has a structure of Formula (VI):

Formula (VI)

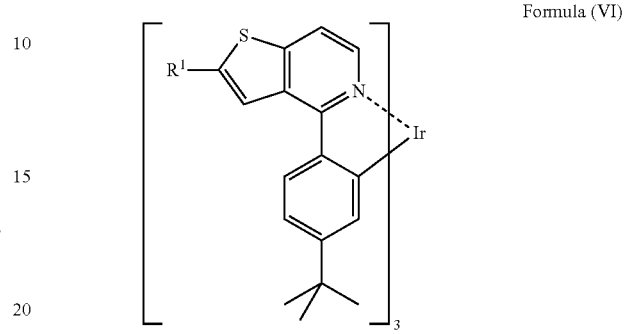

wherein, $R^1$ is $C_{5-10}$ cycloalkyl group, $C_{3-12}$ heteroaryl group, or $C_{6-12}$ aryl group.

10. The organic metal compound as claimed in claim 9, wherein $R^1$ is cyclopentyl group, cyclohexyl group, phenyl group, biphenyl group, or naphthyl group.

11. An organic light-emitting device, comprising:
a pair of electrodes; and
an organic light-emitting element, disposed between the electrodes, wherein the organic light-emitting element comprises the organic metal compound as claimed in claim 1.

12. The organic light-emitting device as claimed in claim 11, wherein the organic light-emitting element comprises a light-emitting layer, wherein the light-emitting layer comprises a host material and the organic metal compound.

* * * * *